US006350868B1

(12) United States Patent
Weston et al.

(10) Patent No.: US 6,350,868 B1
(45) Date of Patent: Feb. 26, 2002

(54) ANTISENSE HUMAN FUCOSYLTRANSFERASE SEQUENCES AND METHODS OF USE THEREOF

(75) Inventors: Brent W. Weston, Durham; Kara M. Hiller, Chapel Hill, both of NC (US)

(73) Assignee: University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 09/556,031

(22) Filed: Apr. 20, 2000

Related U.S. Application Data

(60) Provisional application No. 60/131,068, filed on Apr. 26, 1999.

(51) Int. Cl.[7] .................. C07H 21/04; C12N 15/85; C12N 15/63
(52) U.S. Cl. .................. 536/24.5; 435/320.1; 435/325; 536/23.1; 536/24.5
(58) Field of Search .................. 514/44; 435/6, 435/320.1, 325, 366; 536/23.1, 24.5

(56) References Cited

U.S. PATENT DOCUMENTS

| | | | |
|---|---|---|---|
| 5,324,663 A | * 6/1994 | Lowe | 435/320.1 |
| 5,770,420 A | 6/1998 | Lowe et al. | |
| 5,801,154 A | * 9/1998 | Baracchini et al. | 514/44 |
| 5,827,817 A | 10/1998 | Larsen et al. | |

OTHER PUBLICATIONS

Branch, A good antisense molecule is hard to find, TIBS, vol. 23, pp. 45–50, Feb. 1998.*
Agrawal, Antisense oligonucleotides:towards clinical trials, TIBTECH, vol. 14, pp. 376–387, Oct. 1996.*
Gewirtz et al., Facilitating oligonucleotide delivery: helping antisense deliver on its promise, PNAS, vol. 93, pp. 3161–3163, Apr. 1996.*
Weston et al., Molecular cloning of a fourth member of a human alpha(1, 3)fucosyltransferase gene family, J. Biol. Chem., vol. 267 (34), pp. 24575–24584, Dec. 5, 1992.*
James, W., Towards gene–inhibition therapy: a review of progress and prospects in the field of antiviral antisense nucleic acids and ribozymes, *Antiviral Chemistry & Chemotherapy*, vol. 2, No. 4, pp. 191–214 (1991).
Milner, Natalie, et al., Selecting effective antisense reagents on combinatorial oligonucleotide arrays, *Nature Biotechnology*, vol. 15, pp. 537–541 (Jun. 1997).
International Search Report PCT/US00/10547; dated Oct. 4, 2000.
Weston et al.; Molecular Cloning of a Fourth Member of a Human α(1,3)Fucosyltransferase Gene Family, *The Journal of Biological Chemistry* 267:34 24575–24584 (1992).
McCurley et al.; Physical Maps of Human α(1,3)Fucosyltransferase Genes FUT3–FUT6 on Chromosomes 19p13.3 and 11q21, *Genomics* 26 142–146 (1995).
Cameron et al.; Expression of Human Chromosome 19p α(1,3)–Fucosyltransferase Genes in Normal Tissues, *The Journal of Biological Chemistry* 270:34 20112–20122 (1995).

* cited by examiner

*Primary Examiner*—Andrew Wang
(74) *Attorney, Agent, or Firm*—Myers Bigel Sibley & Sajovec, P.A.

(57) ABSTRACT

The present invention provides oligonucleotides that hybridizes to a nucleic acid that encodes a fucosyltransferase (FUT). The fucosyltransferase is preferably FUT3 or FUT6, along with vectors that contain the same. Pharmaceutical formulations that contain such oligonucleotides or vectors are also provided, along with methods of use thereof in the treatment of cancer.

13 Claims, 9 Drawing Sheets

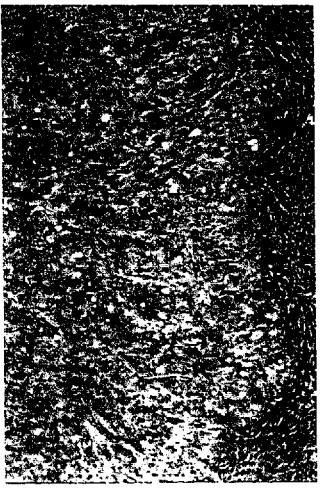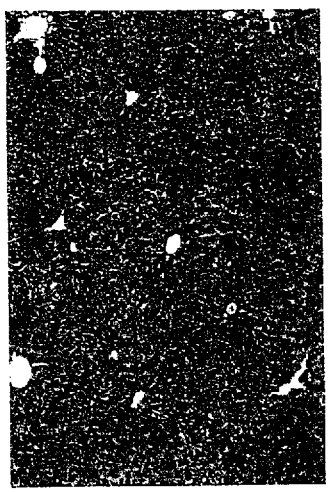
FIG. 7A
FIG. 7B
FIG. 7C
FIG. 7D

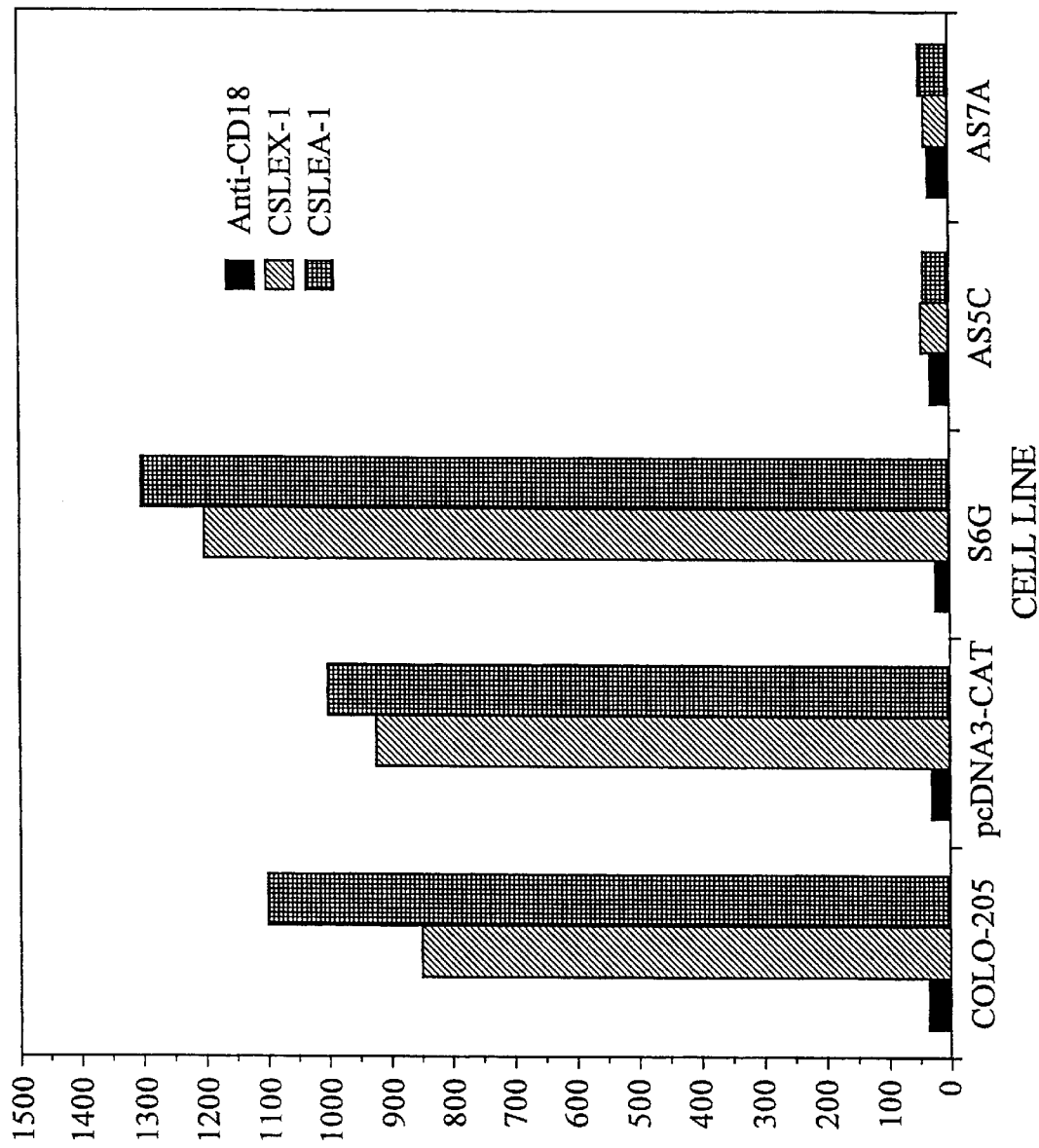

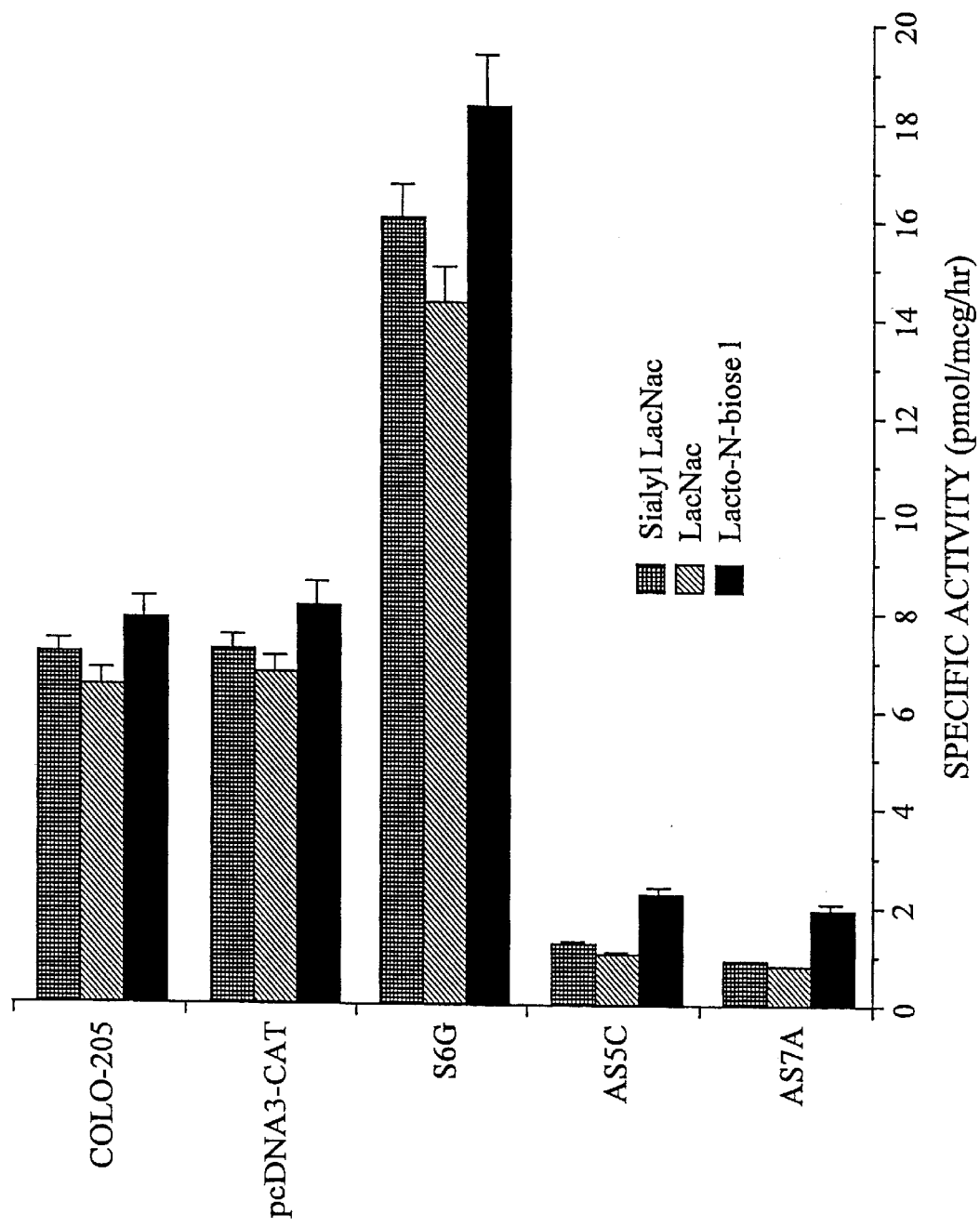

US 6,350,868 B1

ANTISENSE HUMAN FUCOSYLTRANSFERASE SEQUENCES AND METHODS OF USE THEREOF

RELATED APPLICATIONS

This application claims priority from U.S. Provisional Application Serial No. 60/131,068, filed Apr. 26, 1999, the disclosure of which is incorporated by reference herein in its entirety.

STATEMENT OF FEDERAL SUPPORT

This invention was made with Government support under NIH-NCI grant numbers 5K08-CA01758-05 and 1R55-CA755528-01. The Government has certain rights to this invention.

FIELD OF THE INVENTION

The present invention concerns oligonucleotides, including antisense oligonucleotides, that are useful in the treatment of cancer, along with DNA encoding the same, vectors that contain such DNA, cells that express such DNA, pharmaceutical formulations containing the same, and methods of use thereof in the treatment of cancer.

BACKGROUND OF THE INVENTION

Antisense oligonucleotides (along with other oligonucleotides that downregulate gene expression) offer the possibility of targeting a specific gene to study its function, inhibit its product, or repair a defect (A. Gewirtz et al., *Facilitating oligonucleotide delivery: helping antisense deliver on its promise.* Proc. Natl. Acad. Sci. USA, 93: 3161–3163, 1996; L. Long et al., *Loss of the metastatic phenotype in murine carcinoma cells expressing an antisense RNA to the insulin-like growth factor receptor.* Cancer Res., 55: 1006–1009, 1995; H. Sierakowska et al., *Repair of thalassemic human β-globin mRNA in mammalian cells by antisense oligonucleotides.* Proc. Natl. Acad. Sci. USA, 93: 12840–12844, 1996). Antisense is therefore an appealing therapeutic strategy for malignancies, as it avoids some of the widely cytotoxic effects of current cancer therapy (J. Cheng et al., *Amplification of AKT2 in human pancreatic cancer cells and inhibition of AKT2 expression and tumorigenicity by antisense RNA.* Proc. Natl. Acad. Sci. USA, 93: 3636–3641, 1996). Clinically, antisense offers an advantage over antibody-based targeting (T. Kishimoto et al., *Phenotypes correlating to metastatic properties of pancreas adenocarcinoma in vivo: the importance of sialyl Lewis a antigen.* Int. J. Cancer, 69: 290–294, 1996) because the constructs are often less immunogenic and have more favorable pharmacokinetics (J. Phillips et al., *Pharmacokinetics, metabolism, and elimination of a 20-mer phosphorothioate oligodeoxynucleotide (CGP 69846A) after intravenous and subcutaneous administration.* Biochem. Pharmacol., 54: 657–668, 1997). Accordingly, there is a continued need for new oligonucleotides that have anticancer activity.

SUMMARY OF THE INVENTION

A first aspect of the present invention is an oligonucleotide that hybridizes to a nucleic acid that encodes a fucosyltransferase (FUT). The fucosyltransferase is preferably FUT3 or FUT6.

A second aspect of the present invention is a pharmaceutical formulation comprising an oligonucleotide as described above in a pharmaceutically acceptable carrier. The oligonucleotide is included in an amount effective to treat a cancer as described herein, typically from about 0.01 percent to about 99 percent by weight of the formulation.

A third aspect of the present invention is a method of treating a subject afflicted with cancer (e.g., a carcinoma), comprising administering to the subject an oligonucleotide as described above in an amount effective to treat said cancer.

A fourth aspect of the present invention is a nucleic acid encoding an oligonucleotide that hybridizes to a nucleic acid that encodes a fucosyltransferase. The fucosyltransferase is preferably FUT3 or FUT6.

A fifth aspect of the present invention is a vector that contains and expresses a nucleic acid as described above.

A sixth aspect of the present invention is a pharmaceutical formulation comprising a vector as described above in a pharmaceutically acceptable carrier. The vector is included in an amount effective to treat cancer, typically from about 0.01 percent to about 99 percent by weight of the formulation.

A seventh aspect of the present invention is a method of treating a subject afflicted with cancer (e.g., a carcinoma), comprising administering to said subject a vector as described above in an amount effective to treat said cancer.

An eighth aspect of the present invention is a cell that contains and expresses a nucleic acid as described above.

The foregoing and other objects and aspects of the present invention are described in the figures herein and the specification set forth below.

BRIEF DESCRIPTION OF THE DRAWING

FIGS. 7A–7D. Representative microscopic sections (H/E; mag. scale in A) from livers of nude mice injected with HT-29LMM (7A), HT-29LMM/pcDNA3-CAT (7B), LMM/AS1 (7C), and LMM/AS2 (7D) cell lines. Splenic injections were performed as detailed above. Multiple nodules of moderately differentiated colon adenocarcinoma are seen displacing hepatocytes in panels 7A and 7B. No micrometastases were found in multiple sections of liver from animals injected with antisense cell lines LMM/AS1 and LMM/AS2 (panels 7C, 7D, and data not shown).

FIG. 8. Flow cytometry analysis of surface antigens on COLO-205 cells and stable transfectants. Cells were harvested, stained with monoclonal antibodies, and subjected to flow cytometric analysis as described in Materials and Methods. Anti-CD18 results are presented as negative controls. Data presented here are the representative mean fluorescence intensity values from two experiments.

FIG. 9. Fucosyltransferase specific activity of COLO-205 and transfectant cellular extracts. As detailed in Materials and Methods, Triton X-100 detergent extracts prepared from each cell line were assayed for their ability to transfer radiolabeled fucose to low molecular weight carbohydrate acceptors listed in the inset. Control assays with no added acceptor were also performed (data not shown). Fucosyltransferase specific activity is expressed as pmol of fucose transferred per µg extract protein per hour.

DETAILED DESCRIPTION OF PREFERRED EMBODIMENTS

Figure 1:
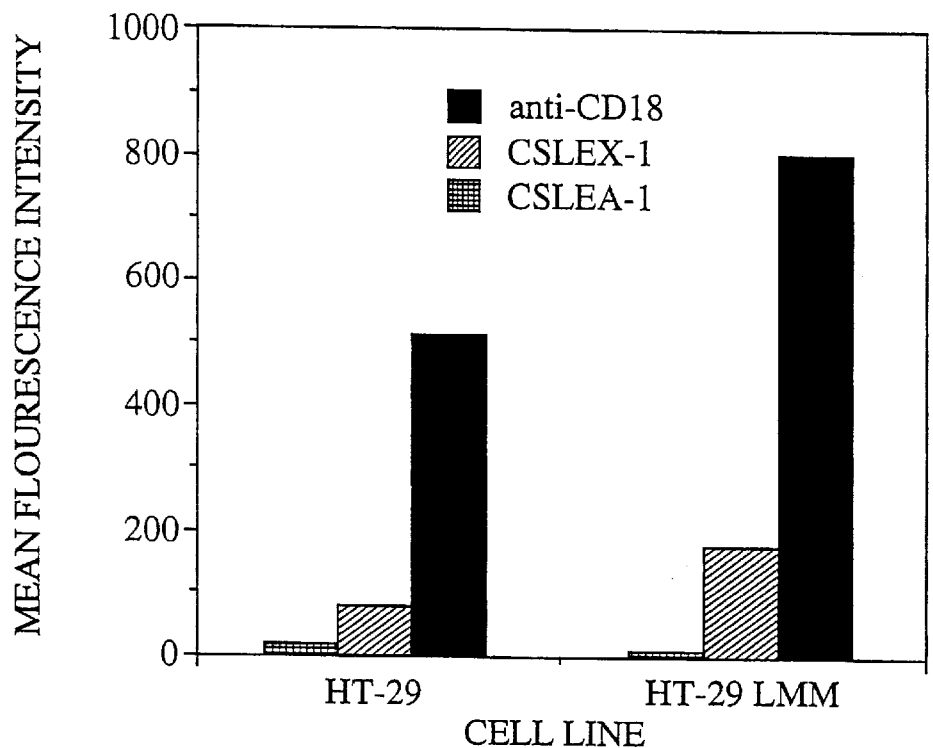
FIG. 1. Flow cytometry analysis of surface antigens on HT-29 and HT-29LMM cells. Cells were harvested, stained with monoclonal antibodies, and subjected to flow cytometric analysis as described in Materials and Methods. Anti-CD18 results are presented as negative controls. Data presented here are representative of the mean fluorescence intensity values from three separate experiments.

Amino acid sequences disclosed herein are presented in the amino to carboxy direction, from left to right. The amino and carboxy groups are not presented in the sequence. Nucleotide sequences are presented herein by single strand only, in the 5' to 3' direction.

The production of cloned genes, recombinant DNA, recombinant vectors, proteins and protein fragments by genetic engineering is well known, and can be carried out in accordance with known techniques. See, e.g., U.S. Pat. No. 5,585,269 to Earp et al.; U.S. Pat. No. 5,468,634 to Liu; and U.S. Pat. No. 5,629,407 to Xiong et al. (the disclosures of all United States Patent references cited herein are to be incorporated herein by reference in their entirety).

The fucosyltransferases FUT 3 and FUT6 referred to herein are known and can be obtained in accordance with known procedures. See, e.g., B. Weston et al., *J. Biol. Chem.* 267, 24575 (1992); R. McCurley et al., *Genomics* 26, 142 (1995); H. Cameron et al., *J. Biol. Chem.* 270, 20112 (1995). The gene may be of any species depending upon the subject and/or the particular use thereof, but is typically mammalian and is preferably human.

The term "target nucleic acid" as used herein refers to a nucleic acid (DNA or RNA) that encodes fucosyltransferase FUT3 or FUT6, as described above.

The term "treat" as used herein refers to any type of treatment that imparts a clinical improvement in the condition of the patient, or delays the progression of the disease.

The term "cancer" as used herein refers to any type of cancer, particularly solid tumors and preferably carcinomas. Specific cancers that may be treated by the method of the invention include colon, pancreatic, ovarian, gastric, breast, lung, heptaocellular, prostate, bladder, renal cell, and uterine cancer. Pancreatic, colon, ovarian and gastric cancer are preferred. And colon and pancreatic cancer are particularly preferred.

While the present invention is primarily concerned with the treatment of human subjects, the invention may also be carried out on animal subjects such as dogs, cats, and horses for veterinary purposes.

1. Oligonucleotides and Administration

The oligonucleotide that binds to the nucleic acid (e.g., DNA, mRNA) may be any oligonucleotide that inhibits the expression of the target gene in cells infected by the vector, such as (i) an antisense oligonucleotide that specifically binds to the mRNA of the target gene to disrupt or inhibit translation thereof, (ii) a ribozyme that specifically binds to the target gene mRNA to disrupt or inhibit translation thereof, (iii) an oligonucleotide that specifically binds to the target nucleic acid duplex to form a triplex and disrupts or inhibits transcription or translation thereof, etc. All of these may be carried out in accordance with known techniques, as (for example) described in U.S. Pat. Nos. 5,650,316; 5,176,996, or 5,650,316 for triplex compounds, in U.S. Pat. Nos. 5,811,537; 5,801,154; and 5,734,039 for antisense compounds, and in U.S. Pat. Nos. 5,817,635; 5,811,300; 5,773,260; 5,766,942; 5,747,335; and 5,646,020 for ribozymnes (the disclosures of which are incorporated by reference herein in their entirety).

The length of the oligonucleotide is not critical so long as the intended function is achieved, but the oligonucleotide is typically from 5, 8, 10, 15, 18 or 20 nucleic acids in length up to 100, 200, 500 or 1000 nucleic acids in length, up to a length equal the full length of the target gene.

The oligonucleotide may be natural (e.g., RNA, DNA) or synthetic (e.g., a phosphorothioate compound). The oligonucleotide may be one that activates RNase H (e.g., and causes cleavage of the target molecules by RNase H) or one that does not activate RNase H (e.g.,and operates by steric hinderance or blocking of the transcription or translation mechanism). Chemical analogs of oligonucleotides with modified or substituted phosphodiester residues, e.g., to the methylphosphonate, the phosphotriester, the phosphorothioate, the phophorodithioate, or the phosphororamidate, may be used. The oligonucleotides may be protected from degredation by adding an end cap which is nuclease resistant, as described in J. Shaw et al., *Nucleic Acids Res.* 19, 747 (1991). The oligonucleotide may be a morpholino oligonucleotide, such as described in J. Summerton and D. Weller, *Antisense & Nucleic Acid Drug Dev.* 7, 187–195 (1997). The design of specific binding sites on the target gene or nucleic acid gene products (e.g., mRNA) may be carried out in accordance with known techniques. For example, the oligonucleotide may be designed to have a sequence that binds to an intron/exon junction, or sufficiently close to an intron/exon junction to inhibit the splicing-out of the intervening exon during processing of precursor mRNA to mature mRNA).

Oligonucleotides that do not activate RNase H can be made in accordance with known techniques. See, e.g., U.S. Pat. No. 5,149,797 to Pederson et al. (The disclosures of all patent references cited herein are to be incorporated herein by reference in their entirety). Such oligonucleotides, which may be deoxyribonucleotide or ribonucleotide sequences, simply contain any structural modification which sterically hinders or prevents binding of RNase H to a duplex molecule containing the oligonucleotide as one member thereof, which structural modification does not substantially hinder or disrupt duplex formation. Because the portions of the oligonucleotide involved in duplex formation are substantially different from those portions involved in RNase H binding thereto, numerous oligonucleotides which do not activate RNase H are available. For example, such oligonucleotides may be oligonucleotides wherein at least one, or all, of the internucleotide bridging phosphate residues are modified phosphates, such as methyl phosphonates, methyl phosphonothioates, phosphoromorpholidates, phosphoropiperazidates and phosphoramidates. For example, every other one of the internucleotide bridging phosphate residues may be modified as described. In another non-limiting example, such antisense oligonucleotides are oligonucleotides wherein at least one, or all, of the nucleotides contain a 2' loweralkyl moiety (e.g., C1–C4, linear or branched, saturated or unsaturated alkyl, such as methyl, ethyl, ethenyl, propyl, 1-propenyl, 2-propenyl, and isopropyl). For example, every other one of the nucleotides may be modified as described. See also P. Furdon et al., *Nucleic Acids Res.* 17, 9193–9204 (1989); S. Agrawal et al., *Proc. Natl. Acad. Sci. USA* 87, 1401–1405 (1990); C. Baker et al., *Nucleic Acids Res.* 18, 3537–3543 (1990); B. Sproat et al., *Nucleic Acids Res.* 17, 3373–3386 (1989); R. Walder and J. Walder, *Proc. Natl. Acad. Sci. USA* 85, 5011–5015 (1988).

The oligonucleotide may function to downregulate expression of the target nucleic acid by upregulating expression of an alternate, non-functional splice variant, in the manner described in U.S. Pat. No. 5,665,593 to Kole.

Figure 11:
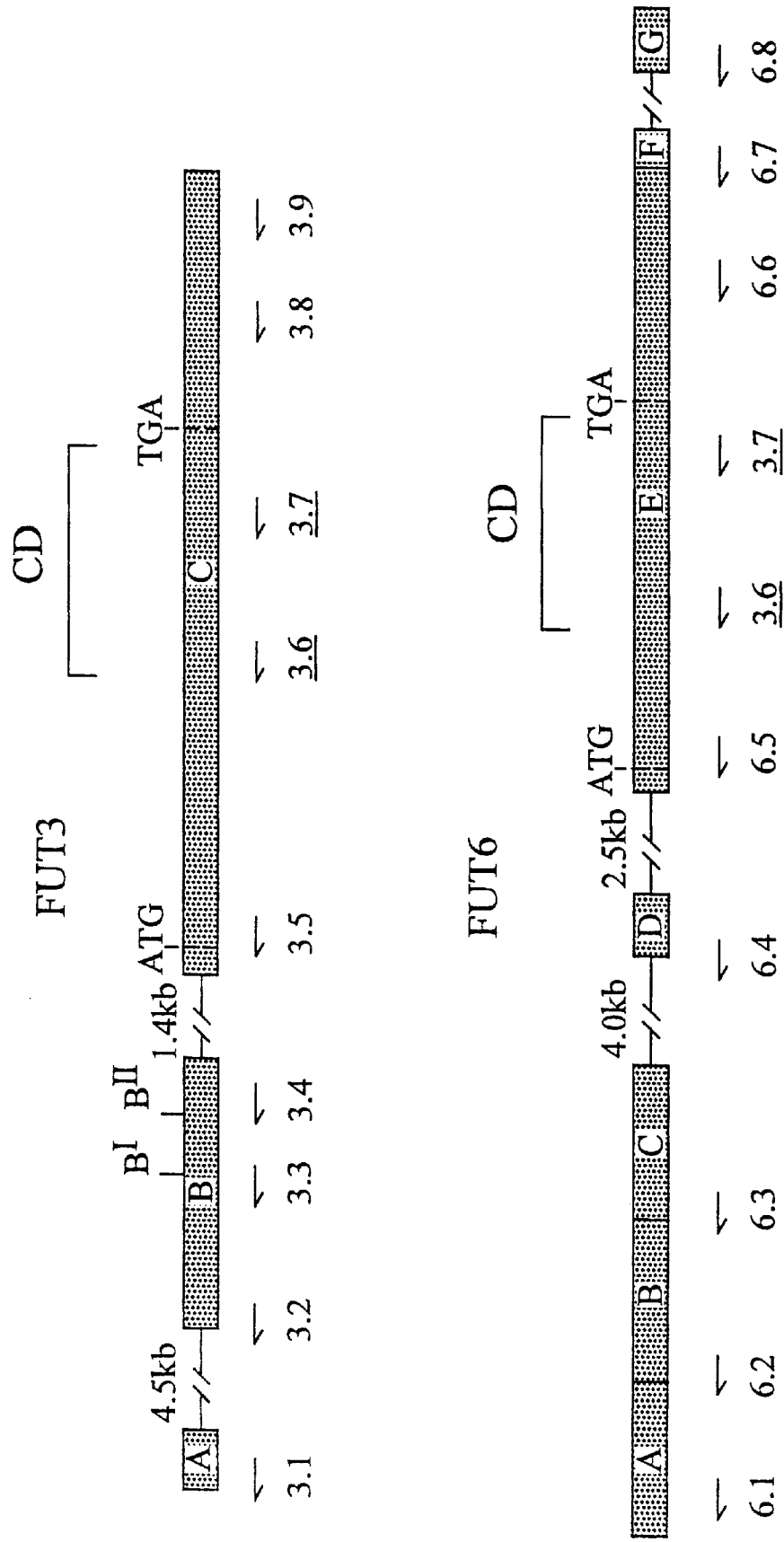
FIG. 11 illustrates FUT3 and FUT6 sequence determinants used for the design of antisense oligonucleotides. Primers 3.1–3.4, 6.1–6.4 and 6.6–6.8 See H. Cameron et al., *J. Biol. Chem* 270, 20112–20122 (1995); Primers 3.8 and 3.9, see B. Weston et al., *J. Biol. Chem.* 267, 24575 (1992); Primers 3.6 and 3.7 (underlined in the Figure) are identical in both genes. "CD" means catalytic domain.

FIG. 11 illustrates FUT3 and FUT6 sequence determinants used for the design of antisense oligonucleotides. Primers 3.1–3.4, 6.1–6.4 and 6.6–6.8 See H. Cameron et al., *J. Biol. Chem* 270, 20112–20122 (1995); Primers 3.8 and 3.9, see B. Weston et al., *J. Biol. Chem.* 267, 24575 (1992); Primers 3.6 and 3.7 (underlined in the Figure) are identical in both genes. "CD" means catalytic domain. Thus, specific examples of antisense oligonucleotides to the FUT3 gene sequence include, but are not limited to, the following 3.1: AGGCCATGGCAGGTTTCCTG (SEQ ID NO: 1)
    3.2: AACTGAAGATCTACAAAAGA (SEQ ID NO: 2)
    3.3: ACCAAGGTTCTGGAAAGAGA (SEQ ID NO: 2)
    3.4: TGTAGGTCACCTGAGTGTGA (SEQ ID NO: 4)
    3.5: GCTGCACCCAGGGGATCCAT (SEQ ID NO: 5)
    3.6: TCTCGTAGTTGCTTCTGCTG (SEQ ID NO: 6)
    3.7: GAGCGAGGCCGCAGCGTCTC (SEQ ID NO: 7)
    3.8: ATCAGCCAGAACCATCACTC (SEQ ID NO: 8)
    3.9: ACCTGTACCCTATAAGTGGT (SEQ ID NO: 9)
    3.A: GATAACTTACCTGGAGAGGC (SEQ ID NO: 10)
    3.B: TTAGGGTTGGACATGATATC (SEQ ID NO: 11)

Specific examples of antisense oligonucleotides to the FUT6 gene sequence include, but are not limited to, antisense oligonucleotides having the following sequences:

6.1: CCCACTCCTGCAGGGCAGTG (SEQ ID NO: 12)
    6.2: GGGTCTTCACCACTGGAGAG (SEQ ID NO: 13)
    6.3: AGTGAAAAGGCTGACCTGAA (SEQ ID NO: 14)
    6.4: TGGATGCCCGTGACACTGGG (SEQ ID NO: 15)
    6.5: GCCGGGCCCAGGGGATCCAT (SEQ ID NO: 16)
    6.6: CACCCAGATCCAGCGTCCCA (SEQ ID NO: 17)
    6.7: ATCTCCTGACCTTGTGATCC (SEQ ID NO: 18)
    6.8: GATCTCCTGACCTAGGAAGA (SEQ ID NO: 19)
    6.A: TTCTCACTCAGTTGGCCCAT (SEQ ID NO: 20)
    6.B: CCAACCACCACACCTGTCAT (SEQ ID NO: 21)
    6.C: GGACGAGTAACAGCTGGATT (SEQ ID NO: 22)

Additional examples of antisense oligonucleotides that may be used to carry out the present invention include, but are not limited to, the following:

GCTTGGCTGCACCCAGGGGATC (SEQ ID NO: 23) (FUT3 3.5); and
    CTCTGCCGCTCCTGGACACTGCTGC (SEQ ID NO: 24) (FUT6 LEADER).

Additional examples of antisense oligonucleotides that can be used to carry out the present invention include any continuous 15 or 18 nucleotide fragment of the sequences listed above.

The term "oligonucleotide" includes the physiologically and pharmaceutically acceptable salts thereof: i.e., salts that retain the desired biological activity of the parent compound and do not impart undesired toxicological effects thereto. Examples of such salts are (a) salts formed with cations such as sodium, potassium, $NH_4^+$, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-oluenesulfonic acid, naphthalenedisulfonic acid, polygalacturonic acid, and the like; and (d) salts formed from elemental anions such as chlorine, bromine, and iodine.

Formulations of the present invention comprise the oligonucleotide in a physiologically or pharmaceutically acceptable carrier, such as an aqueous carrier. Thus, formulations for use in the present invention include, but are not limited to those suitable for parenteral administration, including subcutaneous, intradermal, intramuscular, intravenous and intraarterial administration, as well as topical administration (e.g., administration of an aerosolized formulation of respirable particles to the lungs of a patient). The formulations may conveniently be presented in unit dosage form and may be prepared by any of the methods well known in the art. The most suitable route of administration in any given case may depend upon the subject, the nature and severity of the condition being treated, and the particular active compound that is being used.

The present invention provides for the use of oligonucleotides having the characteristics set forth above for the preparation of a medicament for a patient afflicted with cancer, as discussed above. In the manufacture of a medicament according to the invention, the oligonucleotide is typically admixed with, among other things, an acceptable carrier. The carrier must, of course, be acceptable in the sense of being compatible with any other ingredients in the formulation and must not be deleterious to the patient. The carrier may be a solid or a liquid. One or more oligonucleotides may be incorporated in the formulations of the invention, which may be prepared by any of the well known techniques of pharmacy consisting essentially of admixing the components, optionally including one or more accessory therapeutic ingredients.

Formulations of the present invention may comprise sterile aqueous and non-aqueous injection solutions of the active compound, which preparations are preferably isotonic with the blood of intended recipient and essentially pyrogen free. These preparations may contain anti-oxidants, buffers, bacteriostats and solutes which render the formulation isotonic with the blood of the intended recipient. Aqueous and non-aqueous sterile suspensions may include suspending agents and thickening agents. The formulations may be presented in unit dose or multi-dose containers, for example sealed ampoules and vials, and may be stored in a freeze-dried (lyophilized) condition requiring only the addition of the sterile liquid carrier, for example, saline or water-for-injection immediately prior to use.

In the formulation the oligonucleotide may be contained within a lipid particle or vesicle, such as a liposome or microcrystal, which may be suitable for parenteral administration. The particles may be of any suitable structure, such as unilamellar or plurilamellar, so long as the antisense oligonucleotide is contained therein. Positively charged lipids such as N-[1-(2,3-dioleoyloxi)propyl]-N, N,N-trimethylamoniummethylsulfate, or "DOTAP," are particularly preferred for such particles and vesicles. The preparation of such lipid particles is well known. See, e.g., U.S. Pat. No. 4,880,635 to Janoffet al.; U.S. Pat. No. 4,906,477 to Kurono et al.; U.S. Pat. No. 4,911,928 to Wallach; U.S. Pat. No. 4,917,951 to Wallach; U.S. Pat. No. 4,920,016 to Allen et al.; U.S. Pat. No. 4,921,757 to Wheatley et al.; etc.

The dosage of the oligonucleotide administered will depend upon the particular method being carried out and when it is being administered to a subject, and will further depend on the disease, the condition of the subject, the particular formulation, the route of administration, etc. In general, intracellular concentrations of the oligonucleotide of from 0.05 or 0.2 $\mu$M, to about 5 or 50 $\mu$M, are desired. For administration to a subject such as a human, a dosage of from about 0.01, 0.1, or 1 mg/Kg up to 50, 100, or 150 mg/Kg is employed.

2. Vectors and Vector Administration

Vectors used to carry out the present invention are, in general, RNA virus or DNA virus vectors, such as lentivirus vectors, alphavirus vectors, papovavirus vectors (e.g., SV40 vectors and polyoma vectors), adenovirus vectors and adeno-associated virus vectors. See generally T. Friedmann, Science 244, 1275 16 (June 1989).

Examples of lentivirus vectors that may be used to carry out the present invention include Moloney Murine Leukemia Virus vectors, such as those described in U.S. Pat. No. 5,707,865 to Kohn.

Any adenovirus vector can be used to carry out the present invention. See, e.g., U.S. Pat. Nos. 5,518,913, 5,670,488, 5,589,377; 5,616,326; 5,436,146; and 5,585,362. The adenovirus can be modified to alter or broaden the natural tropism thereof, as described in S. Woo, *Nature Biotechnology* 14, 1538 (Nov. 1996).

Any adeno-associated virus vector (or AAV vector) can also be used to carry out the present invention. See, e.g., U.S. Pat. Nos. 5,681,731; 5,677,158; 5,658,776; 5,658,776; 5,622,856; 5,604,090; 5,589,377; 5,587,308; 5,474,935; 5,436,146; 5,354,678; 5,252,479; 5,173,414; 5,139,941; and 4,797,368.

Alphavirus vectors are known and described in, for example, U.S. Pat. No. 5,811,407 to Johnston et al. and U.S. Pat. No. 5,505,947 to Johnston et al.

The regulatory sequences, or the transcriptional and translational control sequences, in the vectors can be of any suitable source, so long as they effect expression of the heterologous nucleic acid in the target cells. For example, commonly used promoters are the LacZ promoter, and promoters derived from polyoma, Adenovirus 2, and Simian virus 40 (SV40). See, e.g., U.S. Pat. No. 4,599,308.

The heterologous nucleic acid may encode any product that inhibits the expression of the target gene in cells infected by the vector, such as an antisense oligonucleotide that specifically binds to the mRNA of the target gene to disrupt or inhibit translation thereof, a ribozyme that specifically binds to the target gene mRNA to disrupt or inhibit translation thereof, or a triplex nucleic acid that specifically binds to the target gene duplex DNA and disrupts or inhibits transcription thereof, as described above. Again, the length of the heterologous nucleic acid is not critical so long as the intended function is achieved, but the heterologous nucleic acid is typically from 5, 8, 10 or 20 nucleic acids in length up to 100, 200, 500 or 1000 nucleic acids in length, up to a length equal the full length of the target gene.

Once prepared, the recombinant vector can be reproduced by (a) propagating the vector in a cell culture, the cell culture comprising cells that permit the growth and reproduction of the vector therein; and then (b) collecting the recombinant vector from the cell culture, all in accordance with known techniques. The viral vectors collected from the culture may be separated from the culture medium in accordance with known techniques, and combined with a suitable pharmaceutical carrier for administration to a subject. Such pharmaceutical carriers include, but are not limited to, sterile pyrogen-free water or sterile pyrogen-free saline solution. If desired, the vectors may be packaged in liposomes for administration, in accordance with known techniques.

Any suitable route of administration can be used to carry out the present invention, depending upon the particular condition being treated. Suitable routes include, but are not limited to, intravenous, intrarterial, intrathecal, intraperitoneal, intramuscular, and intralesional injection. Intralesional injection is currently preferred.

The dosage of the recombinant vector administered will depend upon factors such as the particular disorder, the particular vector chosen, the formulation of the vector, the condition of the patient, the route of administration, etc., and can be optimized for specific situations. In general, the dosage is from about $10^7$, $10^8$, or $10^9$ to about $10^{11}$, $10^{12}$, or $10^{13}$ plaque forming units (pfu).

In addition to the foregoing, the present invention provides cells, particularly mammalian and most preferably human, cells that contain and express an oligonucleotide as described above. The cells are useful, among other things, for screening oligonucleotides for their ability to bind to the target nucleic acids described herein. Such cells may be transiently or stably transfected; that is, may transiently or stably express the oligonucleotides described herein. Vectors as described above may be employed, or other vectors such as plasmid vectors, in accordance with known techniques.

The present invention is described in further detail in the following non-limiting Examples, in which the following abbreviations are used: Lewis x, Galβ1->4[Fucα1->3]GlcNAc; sLex, sialyl Lewis x, NeuNAcα2->3Galβ1->4[Fucα1->3]GlcNAc; sLea, sialyl Lewis a, NeuNAcα2->3Galβ1->3[Fucα1->4]GlcNAc; LacNAc, N-acetyllactosamine, Galβ1->4GlcNAc; Lacto-N-biose I, Galβ1->3GlcNAc; sialyl LacNAc, α(2,3)sialyl-N-acetyllactosamine, NeuNAcα2->3Galβ1->4GlcNAc; α(1,3) fucosyltransferase, GDP-fucose:β-D-N-acetylglucosaminide 3-α-L-fucosyltransferase; PCR, polymerase chain reaction; RT-PCR, reverse transcriptase-mediated polymerase chain reaction; kb, kilobase; bp, base pair; FBS, fetal bovine serum; TBS, tris-buffered saline; PBS, phosphate-buffered saline; FITC, fluorescein isothiocyanate; HUVEC, human umbilical vein endothelial cell; TNF-α, tumor necrosis factor-α.

EXAMPLE 1

Expression of Human α(1,3)fucosyltransferase Antisense Sequences Inhibits Selectin-mediated Adhesion and Liver Metastasis of Colon Carcinoma Cells The initial steps of leukocyte and tumor cell adhesion involve selectin receptor/ligand interactions. The selectin ligand components sialyl Lewis x and sialyl Lewis a are oncodevelopmental antigens involved in progression of adenocarcinoma. Interrupting biosynthesis of these surface glycans by inhibition of α(1,3)fucosyltransferase (FUT) gene expression is an attractive goal for functional and therapeutic studies. We report here the inhibition of E-selectin-mediated adenocarcinoma cell adhesion by stable transfection of antisense sequences directed at the human Lewis α(1,3/1,4) fucosyltransferase gene, FUT3. The metastatic parental cell line, HT-29LMM, expressed high levels of sialyl Lewis x, sialyl Lewis a, α(1,3/1,4) fucosyltransferase activity, and FUT3 transcript, but antisense transfectant cell lines did not. When injected into the spleens of nude mice, the stable antisense clones were unable to colonize the liver. These results provide target validation for inhibition of carcinoma metastasis with antisense FUT sequences and confirm the primacy of α(1,3) fucosyltransferases in the synthesis of selectin ligands.

A. Materials and Methods

Cell culture. HT-29, HT-29LMM, and human umbilical endothelial cells (HUVEC) were isolated and propagated as previously described (J. Price et al., *Clin. Expl. Metastasis*, 7: 55–68, 1989; K. Yoshida et al., *J. Surg. Oncol.*, 49: 249–252, 1992; L. Romer et al., *Mol. Biol. Cell.*, 5: 349–361, 1994).

Antibodies. Mouse IgG1/IgG2 control and anti-CD18 antibodies were obtained through Becton Dickinson (San Jose, Calif.). Anti-Lewis x antibody (anti-SSEA-1, mouse IgM) was obtained through the Developmental Studies Hybridoma Bank (Iowa City, Iowa). A monoclonal anti-VIM-2 antibody (IgM) was purchased from Immunotech (Westbrook, Me.). Monoclonal anti-sialyl Lewis a antibody (CSLEA-1, mouse IgG3) was a gift from Dr. P. Terasaki (UCLA, Los Angeles) Sources for the anti-sialyl Lewis x IgM monoclonal antibodies CSLEX1 and KM93 were Becton Dickinson and Kamiya Biomedical (Seattle, Wash.), respectively. For blocking studies, anti-E-selectin antibody (CD62E, 1.2B, mouse IgG1) was obtained from Serotec (Raleigh, N.C.). Fluorescein-conjugated goat anti-mouse IgM and IgG antibodies were purchased from Sigma (St. Louis, Mo.).

Flow cytometry analysis. HT-29, HT-29LMM, and cloned cell lines were prepared and stained with monoclonal anti-carbohydrate antibodies at saturating concentrations as described (B. Weston et al., *J. Biol. Chem.*, 267: 4152–4160, 1992; B. Weston et al., *J. Biol. Chem.*, 267: 24575–24584, 1992). Anti-SSEA-1 was used at a dilution of 1:1000 and anti-VIM-2 was used at 1:50. Anti-sialyl Lewis x (CSLEX-1) was used at 10 μg/ml. Anti-sialyl Lewis a (CSLEA-1) was used at 1:500. Cells were then stained with fluorescein isothiocyanate-conjugated goat anti-mouse IgM or anti-mouse IgG. Mouse IgG1/IgG2 and anti-CD18 antibodies (negative controls throughout) were used according to the manufacturer's instructions. Cells were analyzed on a Becton-Dickinson FACScan as previously described (Id.).

Fucosyltransferase assays. Triton X-100 extracts were prepared from HT-29, HT-29LMM, and transfected cells as described (Id.). Fucosyltransforase assays were performed in a volume of 20 μl, and contained 25 mM sodium cacodylate (pH 6.2), 5 mM ATP, 10 mM L-fucose, 20 mM $MnCl_2$, 3 μM GDP-[$^{14}$C]fucose (Amersham), and 10 μg of cell extract protein. Acceptor substrates (N-acetyllactosamine, Galβ1->4GlcNAc; Lacto-N-biose I, Galβ1->3GlcNAc; or α(2,3)sialyl-N-acetyllactosamine, NeuNAcα2->3Galβ1->4GlcNAc) were added to a final concentration of 20 mM. Control assays with no added acceptor were performed using the same conditions. Reactions were incubated at 37° C. for one hour. Assays were terminated with 580 μl of 5 mM sodium phosphate, pH 6.8. The terminated assays were centrifuged and the supernatants were collected. An aliquot of each terminated reaction supernatant was subjected to scintillation counting. Another aliquot was applied to a column containing either Dowex 1X2-400, formate form or a Dowex 1-X8 ($PO4^{-2}$) column equilibrated as previously described (Id.). To quantitate incorporation of radioactive fucose into product, the flow-through fraction and 2 ml of a subsequent water elution were collected, pooled, and counted. A portion of this material was assayed by HPLC as described (Id.).

Sialyltransferase assays. Sialyltransferase assays were performed in a volume of 30 μl, and contained 50 mM Tris-maleate (pH 6.7), 10 mM $MnCl_2$, 0.3 nM CMP-[$^{14}$C]NeuNAc (Amersham), and 10 μg of cell extract protein. Acceptor substrate (N-acetyllactosamine, Galβ1->4GlcNAc, Sigma) was added to a final concentration of 0.1 mM. Control assays with no added acceptor were performed using the same conditions. Reactions were incubated at 37° C. for two hours. Assays were terminated by addition of 30 μl ethanol, followed by addition of 540 μl of distilled water. The terminated assays were desalted over Dowex AG 1 (AC-) and Dowex AG 50 (H+). Neutral saccharides were eluted with 4 ml of water and charged saccharides with 14 ml of 0.5 M acetic acid (M. Majuri et al., *Int. J. Cancer*, 63: 551–559, 1995). An aliquot of each reaction was subjected to scintillation counting. Another aliquot was used for HPLC confirmation of product structure in accordance with known techniques.

RNA isolation. Total cellular RNA was extracted with guanidine isothiocyanate and purified by cesium chloride gradient centrifugation. Poly(A)$^+$RNA was prepared using oligo(dT)-cellulose chromatography (H. Cameron et al., *J. Biol. Chem.*, 270: 20112–20122, 1995).

Northern blot analysis. Poly(A)$^+$ RNA (15 ug, divided into 5 μg per lane) was denatured and separated with 1.2% formaldehyde agarose gel electrophoresis and transferred to Hybond-N membranes (Amersham). The membrane was cut into separate strips, which were then prehybridized for 4 hours at 42° C. Gene-specific probes were constructed as previously described, and hybridization to β-actin message was used as control (S. Natsuka et al., *J. Biol. Chem.*, 269: 16789–16794, 1994; H. Cameron et al., *J. Biol. Chem.*, 270: 20112–20122, 1995; K. Yago et al., *Cancer Res.*, 53: 5559–5565, 1993.). Probes were labeled with [$^{32}$P]dCTP by random priming and purified from unincorporated isotope at a specific activity of $1\times10^9$ cpm/ug or higher (M. Majuri et al., supra.). Hybridization was carried out at 42° C. for 16–20 h. The final wash was carried out at 65° C. with 0.5×SSC and 0.2% SDS for 30 min. Autoradiograms were scanned and the images were sized, grouped, and labeled using Adobe Photoshop 5.0 (Mountain View, Calif.).

RT-PCR analysis. First strand cDNA was prepared using 200 ng of poly(A)$^+$ RNA. Synthesis of cDNA was carried out in a 50 μL reaction volume with 12 U of Moloney murine leukemia virus reverse transcriptase and 125 ng of lower strand cDNA primers (H. Cameron et al., supra). PCR amplifications were performed using the lower strand cDNA primers and previously described FUT3-FUT7 gene-specific upper strand primers and amplification profiles (K. Sasaki et al., *J. Biol. Chem.*, 269: 14730–14737, 1994.; H. Cameron et al., supra). To control for genomic DNA contamination, parallel amplifications of all samples with no reverse transcriptase were performed (data not shown). RT-PCR of human cytoplasmic β-actin was performed with previously reported primers to verify the quality/quantity of RNA and further exclude the possibility of genomic contamination in accordance with known techniques.

Construction of FUT3 antisense, sense, and control plasmids for stable transfection of HT-29LMM. The plasmid pcDNA3 (InVitrogen, Carlsbad, Calif.) was chosen for cloning and selection of FUT3 antisense, sense, and control constructs in HT-29LMM due to preliminary data showing high level expression of chloramphenicol acetyltransferase (CAT) in stable transfection experiments of parental HT-29 cells (data not shown). The CAT coding region (Pharmacia, Piscataway, N.J.) was cloned in the sense orientation into the HindIII site of pcDNA-3 and served as control throughout expression studies. The plasmid pcDNA3-FUT3S was created by digestion of pFUT3 (R. Mollicone et al., *J. Biol. Chem.*, 269: 20987–20994, 1994) with XhoI and XbaI and directional cloning into pcDNA3. Likewise, pFUT3 was also digested with XhoI and HindIII, and the resulting fragment cloned in antisense orientation to the CMV promoter in pcDNA3, yielding the expression vector pcDNA3-FUT3AS. Finally, a truncated coding region antisense construct was created by amplification of FUT3 bp 733–1004 (J. Kukowska-Latallo et al., *Genes Devel.*, 4: 1288–1303, 1990) with the HindIII-containing primers aagcttCTGGCCTTCGAGAACTCCTTGCACC (upper strand, HindIII in lower case) and aagcttAGTGCCCAGCTGAAGGAGCGAGGCC (lower strand). The resulting 272 bp fragment, which corresponds to the putative catalytic domain of FUT3 (Id.), was cloned in reverse orientation into the HindIII site of pcDNA3 to yield the vector pcDNA3-FUT3CD AS (data not shown).

Stable transfection, selection, and cloning of FUT3 antisense and sense HT-29LMM cell lines. Approximately 24 hours before transfection, HT-29LMM cells were plated at a density of 1.30–1.50×10$^6$ cells per 60 mm dish in 5 ml of RPMI-1640 with 10% FBS. In separate tubes, 8 μg of the PvuI-linearized plasmids pcDNA3-CAT, pcDNA3-FUT3S, pcDNA3-FUT3AS, or pcDNA3-FUT3CD AS (above) were mixed with 25 μl of Lipofectamine reagent (GIBCO-BRL, Gaithersburg, Md.) in 200 μl of serum-free media and incubated for 45 minutes at room temperature to allow complex formation. The plates were washed twice with serum-free media, the DNA-liposome complexes were diluted with 800 μl of additional serum-free media, and the dilute complexes were added to each plate. The plates were incubated for 24 hours at 37° C. in 5% $CO_2$. The following day, the serum-free media and unincorporated liposomal complexes were replaced with 5 ml of RPMI-1640 with 10% FBS. Forty-eight hours after transfection, G-418 sulfate (GIBCO-BRL) was added to the medium at a concentration of 1 mg/ml.

After 3–4 weeks in G-418, distinct colonies were observed on each plate and selected with 3 mm cloning cylinders (Fisher, Pittsburgh, Pa.). The colonies were allowed to grow, removed with trypsin, and cloned by limiting dilution in 96 well plates with continued G-418 selection. To assure a homogeneous population, the resulting clones were again subjected to limiting dilution under G-418 selection. Following expansion, cells from each well were subjected to the same expression studies described above. Five clonal sense, five clonal antisense, and three clonal CAT control cell lines were established. Representative clones of each were further characterized for glycan, enzyme, and transcript expression. The two sense clones chosen for study were designated as LMM/S1 and LMM/S2. The two antisense clones selected were LMM/AS1 (transfected with pcDNA3-FUT3AS) and LMM/AS2 (transfected with pcDNA3-FUT3CD AS).

HUVEC adhesion assays. HUVEC, at passage 2, were plated in 30 mm plates and allowed to grow to confluence two days prior to use in cell adhesion assays. Half of the HUVEC plates were incubated with TNFα (20 ng/ml) in medium 199 with 10% fetal bovine serum for 7 hours, while the remaining half were not treated with cytokine. HT-29, HT-29LMM, and transfected cells were washed, fixed, and added to HUVEC monolayers as described (J. Lowe et al., *Cell*, 63: 475–484, 1990). After settling, the cells were incubated on the monolayers for 45 minutes at 6° C. The cells were then removed by gentle aspiration followed by three media washes as described (Id). The number of cells recovered from each plate was determined by counting the pooled washes; the number of bound cells represents the difference between the number of cells applied to each plate and the number recovered from each plate. For blocking with anti-E-selectin antibody, HUVEC were preincubated with 20 μg/ml antibody for 30 minutes at 37° C.

Establishment of hepatic metastases. NCR nu/nu athymic nude mice were obtained from Taconic (Germantown, N.Y.). They were maintained in facilities approved by the American Association for Accreditation of Laboratory Animal Care under specific pathogen-free conditions and fed sterile food and water. Seven- to eight-week-old female nude mice weighing 20–22 gm were anesthetized with intraperitoneal injections of NEMBUTAL™ pentobarbitol. Animals were placed in the supine position and prepared using aseptic technique. Under sterile conditions, a flank incision was made. The spleen was visualized and injected with $1\times10^7$ tumor cells in 100 μl of PBS. The contents were returned to the abdominal cavity and surgical clips were used to close the incision. The mice were allowed to recover and surgical clips were removed from the animals upon complete healing of the laparotomy incision. Liver metastases were grossly evident by 5–7 weeks. Animals were then sacrificed, and liver harvested, examined, and weighed. Livers were harvested from euthanized animals and placed in 10% formalin, and subsequently embedded in paraffin.

B. Results

Figure 2:
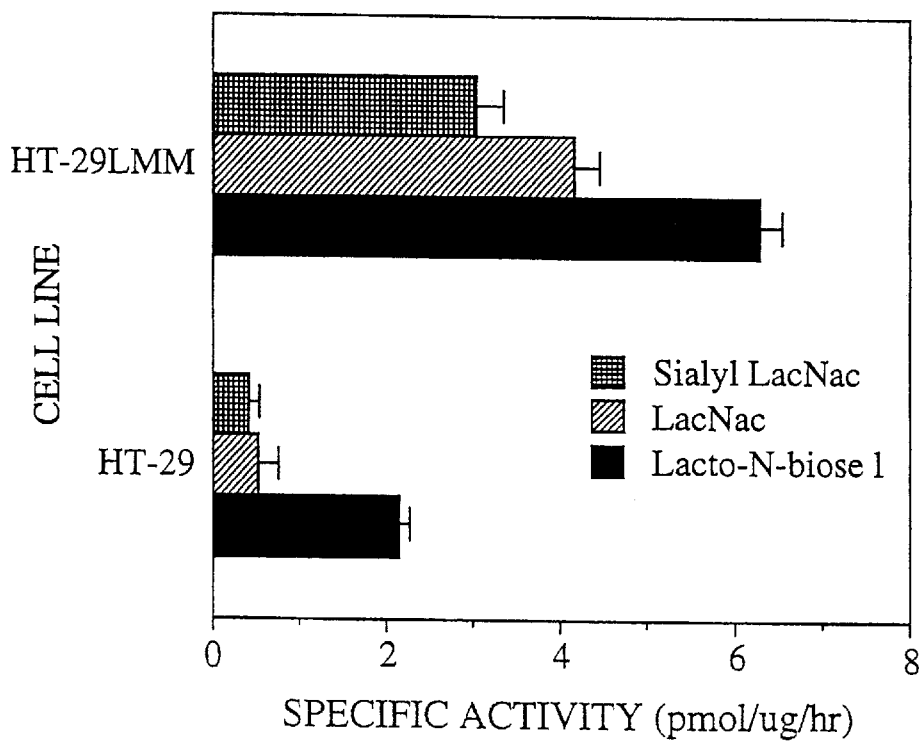
FIG. 2. Fucosyltransferase specific activity of HT-29 and HT-29LMM cellular extracts. As detailed in Materials and Methods, Triton X-100 detergent extracts prepared from each cell line were assayed for their ability to transfer radiolabeled fucose to low molecular weight carbohydrate acceptors listed in the inset. Fucosyltransferase specific activity is expressed as mean pmol of fucose transferred per µg extract protein per hour, +/−standard errors, from four separate determinations.

HT-29LMM cells express higher levels of sialyl Lewis x, sialyl Lewis a, and α(1,3)fucosyltransferase activity than parental HT-29 cells. Results of flow cytometry analyses of surface antigens on HT-29 and HT-29LMM cells are summarized in FIG. 1. HT-29 and HT-29LMM cells do not express high levels of the non-sialylated antigen, Lewis x, or the internally fucosylated antigen, VIM-2 (data not shown). Higher surface levels of the ficosylated and sialylated selectin ligands sialyl Lewis a and sialyl Lewis x are seen on the derived cell line HT-29LMM. Previous reports have documented high expression of dimeric sialyl Lewis x in HT-29LMM (S. Hoff et al., Arch. Surg., 125: 206–209, 1990). To assess if this high level of surface glycan expression was due to corresponding increases in $\alpha(1,3/1,4)$ fucosyltransferase activity, enzyme assays with low molecular weight carbohydrate acceptors were performed. As shown in FIG. 2, cellular extracts from HT-29LMM transferred fucose more efficiently to both type I and type II acceptors (J. Kukowska-Latallo et al., Genes Devel., 4: 1288–1303, 1990) when compared to parental cells. No difference was seen in sialyltransferase activity with HT-29LMM (data not shown). This antigenic and enzymatic profile is consistent with increased expression of Fuc-TIII (J. Kukowska-Latallo et al., *Cell* 63, 1288 (1990); B. Weston, et al., *J. Biol. Chem.* 267, 4152 (1992)) in HT-29LMM.

HT-29LMM cells express higher levels of FUT3 transcript than parental HT-29 cells. To assess whether surface expression of fucosylated ligands is specifically associated with increased expression of FUT3 in HT-29LMM, fucosyltransferase transcript analyses were performed. The results of Northern blot analyses of HT-29 and HT-29LMM cells showed higher levels of FUT3 transcript in the derived cell line (data not shown). RT-PCR analysis of HT-29 and HT-29LMM cells confirms this increase in FUT3 expression (data not shown). Using similar amplification methods (K. Sasaki et al., J. Biol. Chem., 269: 14730–14737, 1994; H. Cameron et al., J. Biol. Chem., 270: 20112–20122, 1995; K. Yago et al., Cancer Res., 53: 5559–5565, 1993), expression of other human fucosyltransferase transcripts is low (FUT4, FUT6, FUT7) or not detectable (FUT5) in both cell lines (data not shown). FUT4-FUT7 transcripts were not detectable by hybridization (data not shown). FUT3 was therefore chosen as the primary target for antisense inhibition studies.

Figure 3:
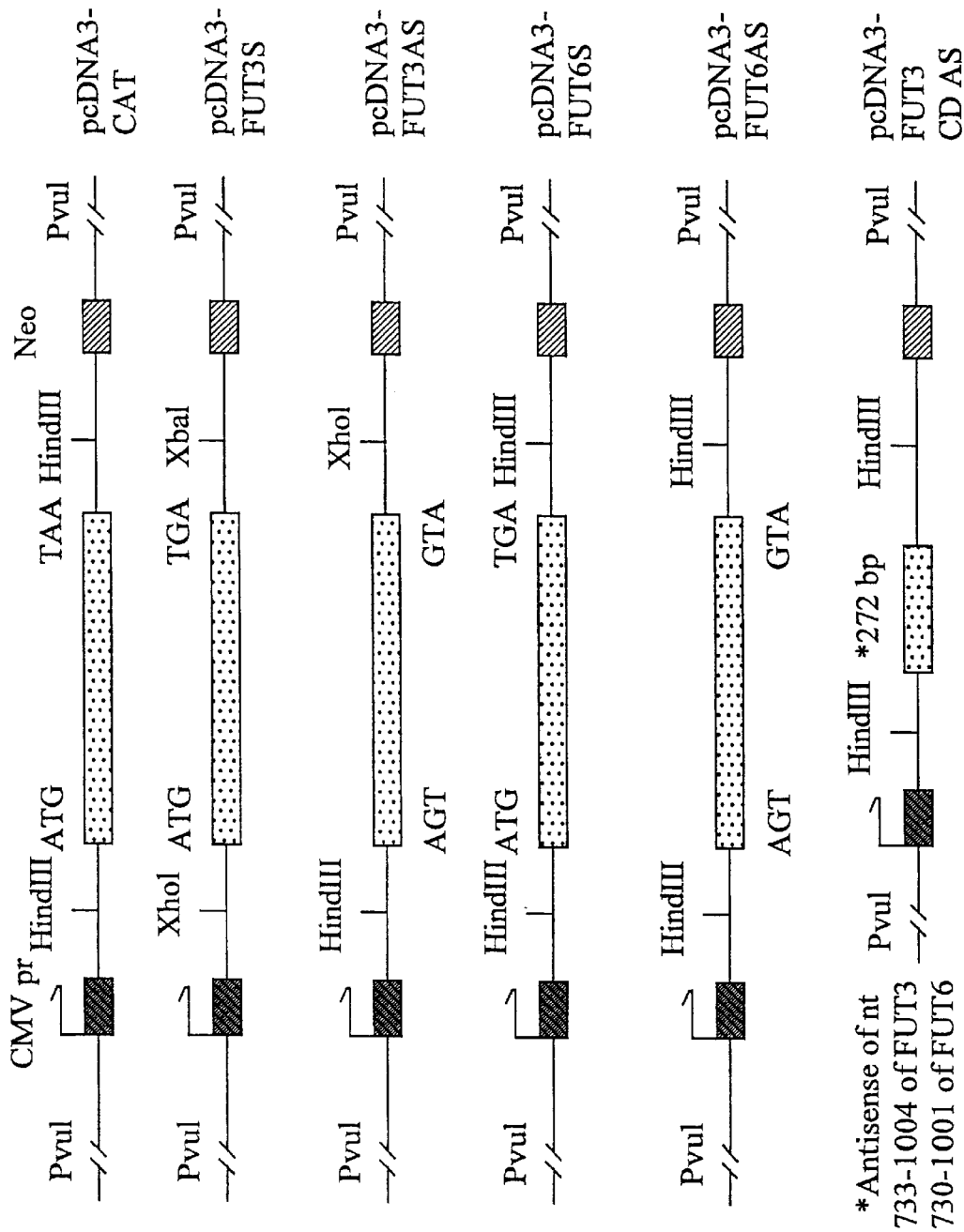
FIG. 3. Constructs used for stable transfection of HT-29LMM cells (Example 1) and COLO-205 cells (Example 2). The expression plasmid pcDNA3 contains a multi-cloning site downstream of the CMV promoter (CMVpr) and upstream of the neomycin resistance sequences (Neo). Constructs were assembled as described in Materials and Methods and linearized with PvuI before transfection.

Characterization of HT-29LMM antisense, sense, and control cell lines. Constructs used for stable transfection of HT-29LMM cells are shown in FIG. 3. The plasmid pcDNA3-CAT was used throughout the following experiments to monitor expression levels over time by CAT assay (data not shown). The plasmid pcDNA3-FUT3S was transfected to allow quantitative comparison of fucosyltransferase activity in cell lines (Table 1) and to serve as an additional control for high level expression over time.

Figure 4:
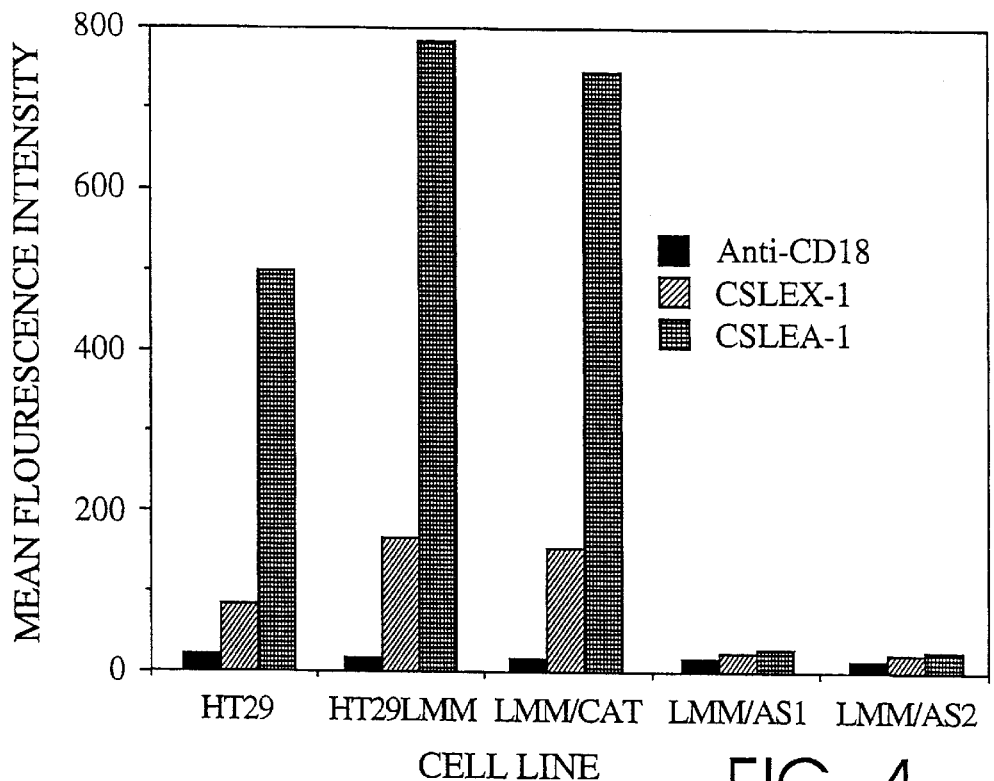
FIG. 4. Flow cytometry analysis of surface antigens on HT-29, HT-29LMM, HT-29LMM/CAT, and stable antisense transfectants LMM/AS1 and LMM/AS2. Cells were harvested, stained with monoclonal antibodies listed in the inset, and subjected to flow cytometric analysis as described (37, 38). Anti-CD18 results are presented as negative controls. Data presented here are representative of the mean fluorescence intensity values from two experiments.

Enzyme assay results in Table 1 show that transfection of the control plasmid pcDNA3-CAT did not affect fucosyltransferase activities. Stable expression of pcDNA3-FUT3S sense constructs in clones LMM/S1 and LMM/S2 enhanced fucosyltransferase activity. In contrast, the cloned antisense cell lines LMM/AS1 and LMM/AS2 had less than 2% specific activity with sialyl LacNac, the trisaccharide precursor for sialyl Lewis x, when compared to untransfected HT-29LMM cells. Furthermore, extracts from LMM/AS1 and LMM/AS2 showed marked reduction in the ability to fucosylate the Type 1 acceptor Lacto-N-biose I. No difference was seen in sialyltransferase activity for any of the cell lines or controls (data not shown). This profile is most consistent with reduced activity of Fuc-TIII in the antisense lines (J. Kukowska-Latallo et al., Genes Devel., 4: 1288–1303, 1990; B. Weston et al., J. Biol. Chem., 267: 4152–4160, 1992). Flow cytometry analyses of surface antigens on HT-29LMM and stable antisense transfectants (FIG. 4) confirm that the synthesis of selectin ligands sialyl Lewis x and sialyl Lewis a is inhibited in LMM/AS1 and LMM/AS2 cells. Northern blot and RT-PCR analyses show that FUT3 transcript levels are markedly reduced in both stable antisense transfectant lines (Table 2).

Figure 5:
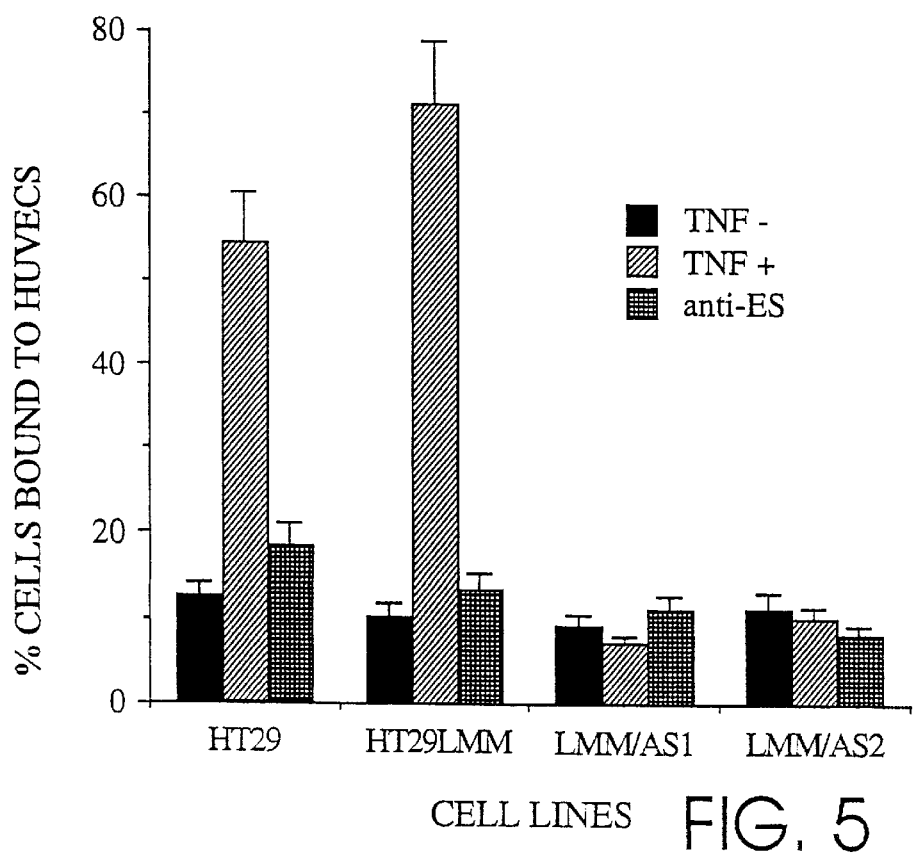
FIG. 5. HT-29LMM and stable antisense transfectant cell line adhesion to human endothelial cells. Each cell line was tested for adhesion to TNF-α stimulated HUVEC (TNF +, striped bars) or untreated HUVEC (TNF –, black bars) as detailed in Materials and Methods. Blocking with anti-E-selectin monoclonal antibody (anti-ES, shaded bars) was performed as described above. The number of bound cells is calculated by subtracting the number of cells recovered (per plate, in pooled washes) from the number of cells applied to each plate. As previously shown (J. Lowe et al., Cell 63, 475 (1990)), background (non-specific) adhesion for this assay is approximately 8–17%; data are the mean values, +/–standard errors, from two separate experiments.
Figure 6A:
FIGS. 6A–6D. Gross appearance of livers from nude mice injected with HT-29LMM (6A), HT-29LMM/pcDNA3-CAT (6B), LMM/AS1 (6C), and LMM/AS2 (6D) cell lines. Splenic injections were performed as detailed in Materials and Methods. Macroscopically, the metastases shown in panels 6A and 6B were observed as multiple irregular gray-white nodules of varying size distributed in both lobes of the liver (n=8 specimens for HT-29LMM). No metastases were seen in livers from mice injected with antisense cell lines LMM/AS1 and LMM/AS2 (n=8 mice for each cell line; see Table 3).
Figure 6B:
Figure 6C:
Figure 6D:

Stable transfection of HT-29LMM with FUT3 antisense constructs inhibits selectin-mediated cell adhesion. To assess whether inhibition of sialyl Lewis x and sialyl a expression on LMM/AS1 and LMM/AS2 was of functional significance, HT29, HT-29LMM and antisense transfectants were assayed for adhesion to human umbilical vein endothelial cells (HUVEC, FIG. 5). Each cell line was tested for adhesion to TNF-a-stimulated HUVEC (striped bars) or untreated HUVEC (black bars) as detailed in Materials and Methods. Blocking with anti-E-selectin monoclonal antibody was performed as described (J. Lowe et al., Cell, 63: 475–484,1990; M. Phillips et al., Science, 250:1130–1132, 1990.). The number of bound cells was calculated by subtracting the number of cells recovered (per plate, in pooled washes) from the number of cells applied to each plate. As summarized in FIG. 5, HT-29LMM cells bound avidly to cytokine-stimulated HUVEC; this binding was specifically inhibited by pre-treatment of HUVEC with anti-E-selectin antibody. The control cell line HT-29LMM/pcDNA3-CAT bound HUVEC with similar affinity (data not shown). Neither antisense cell line was capable of adhering to TNF-$\alpha$-stimulated HUVEC in vitro. These cell lines were chosen for in vivo metastasis studies below.

Stable antisense transfectants of HT-29LMM do not metastasize to liver. Splenic injections of nude mice with HT-29LMM and the antisense transfectant cell lines LMM/AS1 and LMM/AS2 were performed as described in Materials and Methods. Splenic tumors and production of experimental liver metastases were evaluated after 7 weeks. All injected mice developed tumors in the spleen. As shown in Table 3, all 8 mice injected with HT-29LMM developed liver metastases, consistent with previously reported results (S. Hoff et al., Arch. Surg., 125: 206–209, 1990; J. Price et al., Clin. Expl. Metastasis, 7: 55–68, 1989; K. Yoshida et al., J. Surg. Oncol., 49: 249–252, 1992) Average liver replacement by hepatic metastases of HT-29LMM was 48% (range 23–89%) and liver mass increased by approximately 2-fold (Table 3). None of the mice injected with LMM/AS1 or LMM/AS2 transfectants developed hepatic metastasis by gross (FIG. 6) or microscopic (FIG. 7) examination.

TABLE 1

$\alpha(1, 3)$-Fucosyltransferase activity in cellular extracts

| Cells/Constructs | Acceptor | Activity (+/−SD) (pmol/mg/hr) |
|---|---|---|
| HT-29LMM | LacNac | 4070 +/− 292* |
|  | Sialyl-LacNac | 2980 +/− 311 |
|  | Lacto-N-biose I | 6230 +/− 324 |
| HT-29LMM/ | LacNac | 4150 +/− 388 |
| pcDNA3-CAT$^t$ | Sialyl-LacNac | 3300 +/− 275 |
|  | Lacto-N-biose I | 5920 +/− 453 |
| LMM/AS1 | LacNac | 152 +/− 20 |
|  | Sialyl-LacNac | 34 +/− 13 |
|  | Lacto-N-biose I | 85 +/− 41 |
| LMM/AS2 | LacNac | 141 +/− 17 |
|  | Sialyl-LacNac | 46 +/− 32 |
|  | Lacto-N-biose I | 73 +/− 44 |
| LMM/S1 | LacNac | 5510 +/− 477 |
|  | Sialyl-LacNac | 4690 +/− 450 |
|  | Lacto-N-biose I | 7160 +/− 606 |

TABLE 1-continued

α(1, 3)-Fucosyltransferase activity in cellular extracts

| Cells/Constructs | Acceptor | Activity (+/−SD) (pmol/mg/hr) |
| --- | --- | --- |
| LMM/S2 | LacNac | 5025 +/− 221 |
| | Sialyl-LacNac | 4270 +/− 340 |
| | Lacto-N-biose I | 6900 +/− 598 |

*Untransfected HT-29LMM results are from the same assays reported in FIG. 2 (included here for comparison).
†CAT assays performed at same time points show stable expression of plasmid pcDNA3-CAT (data not shown).
HT-29LMM cells were transfected with constructs and methods described in "Experimental Procedures." Fucosyltransferase assays were performed on extracts from transfected cells 28, 56, and 84 days after G-418 selection, cloning, and expansion.

TABLE 2

Quantitation of FUT3 transcript levels in HT-29LMM and antisense clones by Northern blot and RT-PCR.

| Cell line | Expression level relative to β-actin |
| --- | --- |
| HT-29 | 0.2* |
| HT-29LMM | 1.0* |
| LMM/AS1 | <.05 |
| LMM/AS2 | <.05 |

*Comparison data not shown.
PolyA+ RNA from HT-29LMM cells and stable anti-sense transfectants was analyzed as described in "Experimental Procedures." Signal densities were compared using Adobe Photoshop 5.0.

TABLE 3

Liver metastases in nude mice following splenic injection of HT-29LMM cells and stable anti-sense transfectant lines.

| Cells/Constructs | Liver metastases | Liver weights (mean;range) |
| --- | --- | --- |
| HT-29LMM | 8/8 | 2.45 gm (2.00–3.25)* |
| LMM/AS1 | 0/8 | 1.26 gm (1.14–1.38) |
| LMM/AS2 | 0/8 | 1.33 gm (1.15–1.44) | p < .01, HT-29LMM versus LMM/AS1, HT-29LMM versus LMM/AS2.
RT-29LMM cells were transfected with constructs, selected, and characterized for fucosylated glycan expression as described above. $10^7$ tumor cells in 100 μl of PBS were injected into the spleen of an anesthetized nude mouse. The animals were sacrificed 7 weeks post-operatively or when liver metastases were easily palpable.

EXAMPLE 2

Transfection of α(1,3)fucosyltransferase Antisense Sequences Impairs the Proliferative and Tumorigenic Ability of Human Colon Carcinoma Cells Sialyl Lewis x and sialyl Lewis a are oncodevelopmental antigens involved in the pathogenesis of colon adenocarcinoma. Interrupting biosynthesis of these glycans by disruption of α(1,3)fucosyltransferase gene expression is a potential approach to molecular therapy. This example reports the disruption of sialyl Lewis x/a biosynthesis and inhibition of colon carcinoma cell proliferation by stable transfection of antisense sequences directed at the human Lewis α(1,3/1, 4)fucosyltransferase gene, FUT3, and the plasma α(1,3)fucosyltransferase gene, FUT6. COLO-205 cells expressed high levels of sialyl Lewis x/a, α(1,3)fucosyltransferase activity, and FUT3/6 transcripts, but COLO-205-derived antisense transfectant cell lines AS5C and AS7A did not. Sense transfectants S6G expressed higher levels of FUT enzyme and transcript than parental COLO-205. Cellular proliferation assays showed marked correlative decreases in the growth of antisense lines and, conversely, increased growth of sense transfectants. Subcutaneous tumors created by injection of nude mice with antisense transfectant cell lines grew more slowly than those arising from control COLO-205 and sense transfectants. These results provide target validation for inhibition of colon carcinoma proliferation with antisense sequences directed at human FUT genes.

A. Materials and Methods

Cell culture. COLO-205 cells were propagated in RPMI-1640 with 10% FBS.

Antibodies. Antibodies were produced as described in Example 1 above.

Flow cytometry analysis. These procedures were carried out in essentially the same manner as described in Example 1 above, with COLO-205 and cloned cell lines were prepared and stained in like manner as described therein.

Fucosyltransferase assays. Triton X-100 extracts were prepared from parental COLO-205 and transfected cells as described in Example 1 above. Fucosyltransferase assays were performed in a volume of 20 μl, and contained 25 mM sodium cacodylate (pH 6.2), 5 mM ATP, 10 mM L-fucose, 20 mM $MnCl_2$, 3 μM GDP-[$^{14}$C]fucose (Amersham), and 10 μg of cell extract protein. Acceptor substrates (N-acetyllactosamine, Galβ1->4GlcNAc, Lacto-N-biose I, Galβ1->3GlcNAc, or α(2,3)sialyl-N-acetyllactosamine (NeuNAcα2->3Galβ1->4GlcNAc,) were added to a final concentration of 20 mM. Control assays with no added acceptor were performed using the same conditions. Reactions were incubated at 37° C. for one hour. Assays were terminated with 580 μl of 5 mM sodium phosphate, pH 6.8. The terminated assays were centrifuged and the supernatants were collected. An aliquot of each terminated reaction supernatant was subjected to scintillation counting. Another aliquot was applied to a column containing either Dowex™ 1X2-400 (formate form) or a Dowex™ 1-X8 ($PO_4^{-2}$) column equilibrated as described above. To quantitate incorporation of radioactive fucose into product, the flow-through fraction and subsequent water elution were collected, pooled, and counted. A portion of this material was assayed by HPLC as described above.

RNA isolation and Northern blot analyses. Total cellular RNA was extracted with guanidine isothiocyanate and purified by cesium chloride gradient centrifugation. Poly(A)+ RNA was prepared using oligo(dT)-cellulose chromatography, denatured, and separated with 1.2% formaldehyde agarose gel electrophoresis (5 μg per lane) and transferred to Hybond-N™ membranes (Amersham). The membrane was cut into separate strips, which were then prehybridized for 4 hours at 42° C. Gene-specific probes were amplified using previously described PCR conditions and primer sets (H. Cameron et al., J. Biol. Chem., 270: 20112–20122, 1995). Hybridization to β-actin message was used as control (Id.; K. Yago et al., Cancer Res., 53: 5559–5565, 1993). Probes were labeled with [$^{32}$P]dCTP by random priming and purified from unincorporated isotope at a specific activity of $1-10^9$ cpm/ug or higher. Hybridization was carried out at 42° C. for 16–20 h. The final wash was carried out at 65° C. with 0.5×SSC and 0.2% SDS for 30 min. Autoradiograms were scanned and the images were sized, grouped, and labeled using Adobe Photoshop 5.0 (Mountain View, Calif.).

Construction of antisense, sense, and control plasmids for stable transfection of COLO-205. The plasmid pcDNA3

(InVitrogen, Carlsbad, Calif.) was chosen for cloning and selection of antisense, sense, and control constructs in COLO-205 due to data showing high level expression of chloramphenicol acetyltransferase (CAT) in previous transfections (data not shown). The CAT coding region (Pharmacia, Piscataway, N.J.) was cloned in the sense orientation into the HindIII site of pcDNA-3 and served as control throughout expression studies. The plasmid pcDNA3-FUT3S was created by digestion of pFUT3 (R. Mollicone et al., J. Biol. Chem., 269: 20987–20994, 1994) with XhoI and XbaI and directional cloning into pcDNA3. Likewise, pFUT3 was also digested with AhoI and HindIII, and the resulting fragment cloned in antisense orientation to the CMV promoter in pcDNA3, yielding the expression vector pcDNA3-FUT3AS. The FUT6 sense plasmid pcDNA3-FUT6S and antisense plasmid pcDNA3-FUT6AS were constructed by HindIII digestion of pcDNA1-Fuc-TVI (H. Cameron et al., J. Biol. Chem., 270: 20112–20122, 1995) and cloning of the insert (with opposite orientations) into pcDNA3. Finally, a truncated coding region antisense construct was created by amplification of FUT3 bp 733–1004 as described in Example 1 above. The resulting 272 bp fragment, which corresponds to the putative catalytic domain of FUT3 (j. Kukowska-Latallo et al., *Genes Devel.* 4, 1288 (1990)) and FUT6 (B. Weston et al., *J. Biol. Chem.* 267, 4152 (1992)), was cloned in reverse orientation in the HindIII site of pcDNA3 to yield the vector pcDNA3-FUT3CD AS, as described in Example 1 above.

Stable transfection, selection, and cloning of FUT3/FUT6 antisense and sense cell lines. Approximately 24 hours before transfection, COLO-205 cells were plated at 50% confluence in flasks containing RPMI-1640 with 10% FBS. Cells were harvested and washed twice with PBS. In separate 4 mm gap cuvettes (Bio-Rad), 30 µg of the PvuI-linearized plasmids pcDNA3-CAT, pcDNA3-FUT3S, pcDNA3-FUT3AS, pcDNA3-FUT6S, pcDNA3-FUT6AS, or pcDNA3-FUT3CD AS (above and FIG. 4) were mixed with $10^7$ cells in 500 µl of serum-free media and incubated for 10 minutes on ice. The cuvettes were then subjected to electroporation with $V_O$=380 volts and capacitance=1000 µF on a Gene Pulser II apparatus (Bio-Rad). Following electroporation, the cells were immediately plated in 10 ml of RPMI-1640 with 10% FBS in 100 mm plates and incubated at 37° C. in 5% $CO_2$.

Forty-eight hours after transfection, G-418 sulfate (GIBCO-BRL) was added to the medium at a concentration of 1 mg/ml. At 3–4 weeks in G-418, distinct colonies were observed on each plate and selected with 3 mm cloning cylinders (Fisher, Pittsburgh, Pa.). The colonies were cloned by limiting dilution in 96 well plates with continued G-418 selection. To assure a homogeneous population, the resulting clones were again subjected to limiting dilution under G-418 selection. Four clonal sense, four clonal antisense, and three clonal CAT control cell lines were established. Representative clones of each were further characterized for glycan, enzyme, and transcript expression. The sense clone chosen was designated as S6G (transfected with pcDNA3-FUT3S and pcDNA3-FUT6S). The two antisense clones selected were AS5C (transfected with pcDNA3-FUT3AS and pcDNA3-FUT6AS) and AS7A (transfected with pcDNA3-FUT3CD AS).

Proliferation and apoptosis assays. The proliferative ability of transfectants and controls was first measured in RPMI-1640 supplemented with 10% FBS. Transfectants were maintained in G-418 as described above. Cells were seeded at a concentration of $10^4$ cells/cm². Medium renewal was performed every two days. A flask from each combination was harvested daily, and cell yield was determined. Due to its slower growth rate, additional flasks of clone AS7A were harvested at each time point. For anchorage-independent proliferation (AIP) assays, cells were plated at 50,000 cells per 60 mm dish in 0.33% Noble agar (DIFCO) over a 7 ml base layer of 0.5% agar. The medium was supplemented with 5 µM putrescine and 0.1 µg/ml DEAE-dextran (Sigma). One milliliter of medium was added to the dishes every week. Colony-forming efficiency (CFE) was determined after four weeks. For apoptosis assays, transfectants and controls were harvested for flow cytometry as described (B. Weston et al., J. Biol. Chem., 267: 4152–4160, 1992). Annexin V and propidium iodide staining were performed according to the manufacturer's protocol (R&D Systems) and unfixed cells were immediately analyzed. Experiments were performed twice for each cell line, n=3 for each experiment (with the exception of clone AS7A, n=2 for each experiment).

Tumorigenicity assays. NCR nu/nu athymic nude mice were obtained from Taconic (Germantown, N.Y.). Eight-week-old female nude mice weighing 20–22 gm were injected subcutaneously with $10^7$ cells in 100 µl PBS per flank site. Animals were monitored for tumor size over six to eight weeks or until the mass reached 1.5 cm in diameter. The animals were then sacrificed and the tumors harvested, examined, and weighed.

B. Results

COLO-205 cells express high levels of sialyl Lewis x, sialyl Lewis a, α(1,3)fucosyltransferase activity, and FUT3/FUT6 transcripts. Results of flow cytometry analyses of surface antigens on COLO-205 cells are summarized in FIG. 8. COLO-205 cells do not express high levels of the non-sialylated antigen, Lewis x, or the internally fucosylated antigen, VIM-2 (data not shown). High surface levels of the fucosylated and sialylated selectin ligands sialyl Lewis a and sialyl Lewis x are noted. To assess α(1,3/1,4) fucosyltransferase activity, enzyme assays with low molecular weight carbohydrate acceptors were performed as described above. As shown in FIG. 9, cellular extracts from COLO-205 transferred fucose efficiently to both type I and type II acceptors. Northern blot analyses of COLO-205 cells were carried out (data not shown). Probes specific for FUT3 and FUT6 (H. Cameron et al., J. Biol. Chem., 270: 20112–20122, 1995) show high levels of transcript in the parental cell line. Using similar conditions, expression of other human fucosyltransferase transcripts is low (FUT4) or not detectable (FUT5 and FUT7) (data not shown). This antigenic, enzymatic, and transcript expression profile is consistent with high levels of Fuc-TIII and Fuc-TVI in COLO-205. FUT3 and FUT6 were therefore chosen as the primary targets for antisense inhibition experiments.

Characterization of FUT expression in COLO-205 antisense, sense, and control cell lines. Constructs used for stable transfection of COLO-205 cells are shown in FIG. 3. The plasmid pcDNA3-CAT was used throughout the following experiments to monitor expression levels over time by CAT assay (data not shown). Enzyme assay results in FIG. 9 show that transfection of the control plasmid pcDNA3-CAT did not affect fucosyltransferase activities. Stable expression of pcDNA3-FUT3S and pcDNA3-FUT6S sense constructs in clone S6G enhanced fucosyltransferase activity. In contrast, the cloned antisense cell lines AS5C and AS7A had less than 2% specific activity with sialyl LacNac, the trisaccharide precursor for sialyl Lewis x, when compared to untransfected COLO-205 cells. Furthermore, extracts from antisense clones showed marked reduction in the ability to fucosylate the Type I acceptor Lacto-N-biose I. Flow cytometry analyses of surface antigens on COLO-205 and stable antisense transfectants (FIG. 8) confirmed that the synthesis of sialyl Lewis x and sialyl Lewis a is inhibited in the antisense clones. Northern blot analyses show that FUT3 and FUT6 transcript levels are markedly reduced in both stable antisense transfectant lines (data not shown).

Figure 10:
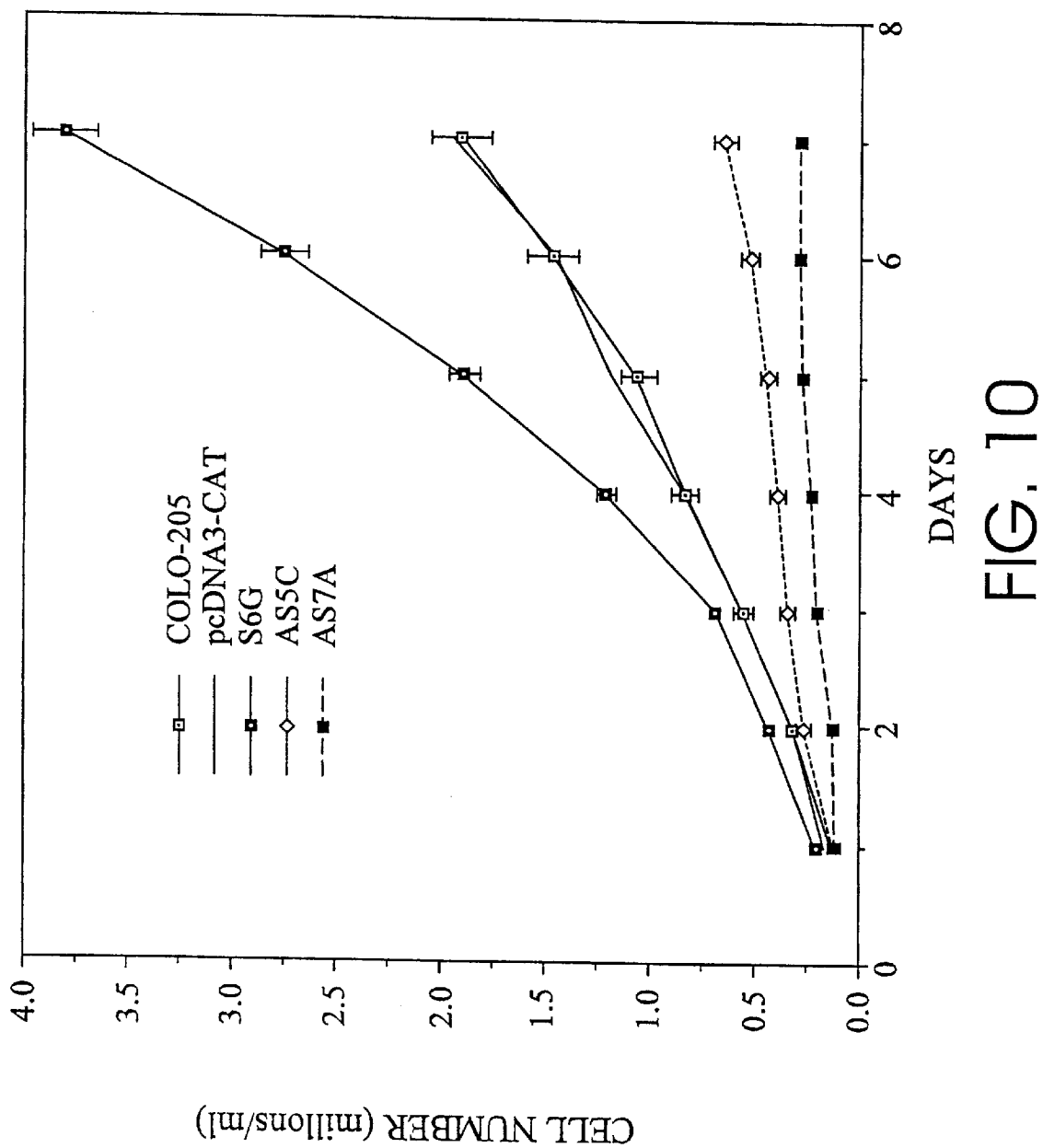
FIG. 10. Proliferative rate of COLO-205 and transfectant cell lines in RPMI with 10% FBS. For clarity, error bars are not shown for pcDNA3-CAT transfectants. Antisense transfectants AS5C and AS7A (dotted lines) grew 3- to 7-fold slower than parental COLO-205 at day 7.

Proliferation of antisense-transfected cells is impaired. The proliferative ability of control, sense, and antisense transfectants was compared in media containing 10% FBS. The growth rate of parental (untransfected) and control (pcDNA3-CAT-transfected) COLO-205 cells was similar (FIG. 10). Sense clone S6G grew at a notably higher rate, while antisense cell line AS5C grew more slowly than control. Antisense AS7A proliferated at such a slow rate that additional cells were maintained just to allow expression studies to be performed (FIG. 10). Representative photomicrographs of G-418-selected colonies at day 28 were taken (not shown); no definite change in morphology of the transfectants is noted. Anchorage independent proliferation (AIP) was inhibited by expression of antisense FUT constructs (Table 4). Conversely, AIP of sense transfectants was higher than control transfectants and parental COLO-205. Flow cytometric analyses of control, sense, and antisense lines showed no differences in the proportions of apoptotic (annexin-V-positive) or non-viable (propidium-iodide-positive) cells (data not shown).

COLO-205 cells transfected with FUT3/FUT6 antisense sequences are less tumorigenic in nude mice. The results of in vivo growth assays employing flank injections of nude mice with control and transfectant cell lines are summarized in Table 5. Parental (untransfected) COLO-205 are highly tumorigenic (T. Kuo et al., Proc. Natl. Acad. Sci. USA, 92: 12085–12089, 1995). Sense transfectants showed slightly higher growth rates in this assay, although the number of mice injected was small for comparisons. Antisense transfectant lines AS5C and AS7A grew at markedly slower rates during the course of the study. These data indicate that expression of antisense FUT sequences is capable of inhibiting colon carcinoma growth in vivo.

TABLE 4

Anchorage-independent proliferation of COLO-205 and transfectant cell lines.

| Cell line | CFB (%) |
| --- | --- |
| COLO-205 | 10.7 +/− 1.2 |
| pcDNA3-CAT | 12.0 +/− 1.5 |
| S6G | 26.8 +/− 3.3 |
| AS5C | 3.46 +/− 0.7 |
| AS7A | 2.72 +/− 0.7* |

*n = 2 for both experiments (n = 3 for other lines).

Colony-forming efficiency (CFE) is reported as the mean +/− SD of the pooled observations from both experiments.

TABLE 5

Tumorigenieity of COLO-205 and transfectant cell lines.

| Cells injected | # Mice | Tumor wts. (mg) |
| --- | --- | --- |
| COLO-205 | 3 | 470 (433–504) |
| S6G | 4 | 682 (605–740) |
| AS5C | 3 | 48 (30–78) |
| AS7A | 3 | 35 (0–80) |

Cells were injected subcutaneously in nude mice as described in Materials and Methods. Tumors were harvested and weighed at six to eight weeks or when 1.5 cm in diameter. Weights are reported as average milligrams (mg) and range.

The foregoing is illustrative of the present invention, and is not to be construed as limiting thereof. The invention is defined by the following claims, with equivalents of the claims to be included therein.

We claim:

1. An oligonucleotide that hybridizes to a nucleic acid that encodes a fulcosyltransferase, wherein said fucosyltransferase is selected from the group consisting of FUT3 and FUT6;

said oligonucleotide selected from the group consisting of oligonucleotides consisting of the sequence:
AGGCCATGGCAGGTTTCCTG (SEQ ID NO: 1);
AACTGAAGATCTACAAAAGA (SEQ ID NO: 2);
ACCAAGGTTCTGGAAAGAGA (SEQ ID NO: 3);
TGTAGGTCACCTGAGTGTGA (SEQ ID NO: 4);
GCTGCACCCAGGGGATCCAT (SEQ ID NO: 5);
TCTCGTAGTTGCTTCTGCTG (SEQ ID NO: 6);
GAGCGAGGCCGCAGCGTCTC (SEQ ID NO: 7);
ATCAGCCAGAACCATCACTC (SEQ ID NO: 8);
ACCTGTACCCTATAAGTGGT (SEQ ID NO: 9);
GATAACTTACCTGGAGAGGC (SEQ ID NO: 10);
TTAGGGTTGGACATGATATC (SEQ ID NO: 11);
CCCACTCCTGCAGGGCAGTG (SEQ ID NO: 12);
GGGTCTTCACCACTGGAGAG (SEQ ID NO: 13);
AGTGAAAAGGCTGACCTGAA (SEQ ID NO: 14);
TGGATGCCCGTGACACTGGG (SEQ ID NO: 15);
GCCGGGCCCAGGGGATCCAT (SEQ ID NO: 16);
CACCCAGATCCAGCGTCCCA (SEQ ID NO: 17);
ATCTCCTGACCTTGTGATCC (SEQ ID NO: 18);
GATCTCCTGACCTAGGAAGA (SEQ ID NO: 19);
TTCTCACTCAGTTGGCCCAT (SEQ ID NO: 20);
CCAACCACCACACCTGTCAT (SEQ ID NO: 21);
GGACGAGTAACAGCTGGATT (SEQ ID NO: 22);
GCTTGGCTGCACCCAGGGGATC (SEQ ID NO: 23);
CTCTGCCGCTCCTGGACACTGCTGC (SEQ ID NO: 24);

and continuous 15 or 18 nucleotide fragments of the sequences listed above.

2. An oligonucleotide according to claim 1, which oligonucleotide activates RNase H.

3. An oligonucleotide according to claim 1, that hybridizes to a nucleic acid that encodes a fucosyltransferase, wherein said fucosyltransferase is selected from the group consisting of FUT3 and FUT6, which oligonucleotide does not activate RNase H.

4. An oligonucleotide according to claim 1 selected from the group consisting of FUT3 antisense oligonucleotides consisting of the sequence:

AGGCCATGGCAGGTTTCCTG (SEQ ID NO: 1);
AACTGAAGATCTACAAAAGA (SEQ ID NO: 2);
ACCAAGGTTCTGGAAAGAGA (SEQ ID NO: 3);
TGTAGGTCACCTGAGTGTGA (SEQ ID NO: 4);
GCTGCACCCAGGGGATCCAT (SEQ ID NO: 5);
TCTCGTAGTTGCTTCTGCTG (SEQ ID NO: 6);
GAGCGAGGCCGCAGCGTCTC (SEQ ID NO: 7);
ATCAGCCAGAACCATCACTC (SEQ ID NO: 8);
ACCTGTACCCTATAAGTGGT (SEQ ID NO: 9);
GATAACTTACCTGGAGAGGC (SEQ ID NO: 10); and
TTAGGGTTGGACATGATATC (SEQ ID NO: 11).

5. An oligonucleotide according to claim 1 selected from the group consisting of FUT6 antisense oligonucleotides consisting of the sequence:

CCCACTCCTGCAGGGCAGTG (SEQ ID NO: 12);
GGGTCTTCACCACTGGAGAG (SEQ ID NO: 13);
AGTGAAAAGGCTGACCTGAA (SEQ ID NO: 14);
TGGATGCCCGTGACACTGGG (SEQ ID NO: 15);
GCCGGGCCCAGGGGATCCAT (SEQ ID NO: 16);
CACCCAGATCCAGCGTCCCA (SEQ ID NO: 17);
ATCTCCTGACCTTGTGATCC (SEQ ID NO: 18);
GATCTCCTGACCTAGGAAGA (SEQ ID NO: 19);
TTCTCACTCAGTTGGCCCAT (SEQ ID NO: 20);
CCAACCACCACACCTGTCAT (SEQ ID NO: 21); and
GGACGAGTAACAGCTGGATT (SEQ ID NO: 22).

6. A composition comprising an oligonucleotide according to claim 1 in a pharmaceutically acceptable carrier;
wherein said oligonucleotide is an oligonucleotide that hybridizes to a nucleic acid that encodes a fucosyltransferase, wherein said fucosyltransferase is selected from the group consisting of FUT3 and FUT6.

7. An exogenous nucleic acid encoding an antisense oligonucleotide that hybridizes to an endogenous nucleic acid that encodes a fucosyltransferase, wherein said fucosyltransferase is selected from the group consisting of FUT3 and FUT6 and wherein said nucleic acid is selected from the group consisting of:

AGGCCATGGCAGGTTTCCTG (SEQ ID NO: 1);
AACTGAAGATCTACAAAAGA (SEQ ID NO: 2);
ACCAAGGTTCTGGAAAGAGA (SEQ ID NO: 3);
TGTAGGTCACCTGAGTGTGA (SEQ ID NO: 4);
GCTGCACCCAGGGGATCCAT (SEQ ID NO: 5);
TCTCGTAGTTGCTTCTGCTG (SEQ ID NO: 6);
GAGCGAGGCCGCAGCGTCTC (SEQ ID NO: 7);
ATCAGCCAGAACCATCACTC (SEQ ID NO: 8);
ACCTGTACCCTATAAGTGGT (SEQ ID NO: 9);
GATAACTTACCTGGAGAGGC (SEQ ID NO: 10);
TTAGGGTTGGACATGATATC (SEQ ID NO: 11);
CCCACTCCTGCAGGGCAGTG (SEQ ID NO: 12);
GGGTCTTCACCACTGGAGAG (SEQ ID NO: 13);
AGTGAAAAGGCTGACCTGAA (SEQ ID NO: 14);
TGGATGCCCGTGACACTGGG (SEQ ID NO: 15);
GCCGGGCCCAGGGGATCCAT (SEQ ID NO: 16);
CACCCAGATCCAGCGTCCCA (SEQ ID NO: 17);
ATCTCCTGACCTTGTGATCC (SEQ ID NO: 18);
GATCTCCTGACCTAGGAAGA (SEQ ID NO: 19);
TTCTCACTCAGTTGGCCCAT (SEQ ID NO: 20);
CCAACCACCACACCTGTCAT (SEQ ID NO: 21);
GGACGAGTAACAGCTGGATT (SEQ ID NO: 22);
GCTTGGCTGCACCCAGGGGATC (SEQ ID NO: 23);
CTCTGCCGCTCCTGGACACTGCTGC (SEQ ID NO: 24);

and continuous 15 or 18 nucleotide fragments of the sequences listed above.

8. An exogenous nucleic acid according to claim 7, wherein said nucleic acid is selected from the group consisting of DNA and RNA.

9. A vector that contains and expresses an exogenous nucleic acid according to claim 7.

10. A composition comprising a vector according to claim 9 in a pharmaceutically acceptable carrier.

11. An isolated cell that contains and expresses a nucleic acid according to claim 7.

12. An oligonucleotide according to claim 1 consisting of the sequence:

GCTTGGCTGCACCCAGGGGATC (SEQ ID NO: 23) (FUT3 3.5).

13. An oligonucleotide according to claim 1 consisting of the sequence:

CTCTGCCGCTCCTGGACACTGCTGC (SEQ ID NO: 24)(FUT 6 LEADER).

* * * * *

SEQUENCE LISTING

```
<160> NUMBER OF SEQ ID NOS: 24

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:antisense
      oligonucleotide

<400> SEQUENCE: 1
aggccatggc aggtttcctg                                                     20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:antisense
      oligonucleotide

<400> SEQUENCE: 2
```
aactgaagat ctacaaaaga                                                20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:antisense
      oligonucleotide

<400> SEQUENCE: 3
accaaggttc tggaaagaga                                                20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:antisense
      oligonucleotide

<400> SEQUENCE: 4
tgtaggtcac ctgagtgtga                                                20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:antisense
      oligonucleotide

<400> SEQUENCE: 5
gctgcaccca ggggatccat                                                20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:antisense
      oligonucleotide

<400> SEQUENCE: 6
tctcgtagtt gcttctgctg                                                20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:antisense
      oligonucleotide

<400> SEQUENCE: 7
gagcgaggcc gcagcgtctc                                                20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:antisense
      oligonucleotide

<400> SEQUENCE: 8
atcagccaga accatcactc                                                20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:antisense
      oligonucleotide

<400> SEQUENCE: 9
acctgtaccc tataagtggt                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:antisense
      oligonucleotide

<400> SEQUENCE: 10
gataacttac ctggagaggc                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:antisense
      oligonucleotide

<400> SEQUENCE: 11
ttagggttgg acatgatatc                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:antisense
      oligonucleotide

<400> SEQUENCE: 12
cccactcctg cagggcagtg                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:antisense
      oligonucleotide

<400> SEQUENCE: 13
gggtcttcac cactggagag                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence:antisense
      oligonucleotide

<400> SEQUENCE: 14
agtgaaaagg ctgacctgaa                                              20

```
<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence:antisense
      oligonucleotide

<400> SEQUENCE: 15
tggatgcccg tgacactggg                                                     20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:antisense
      oligonucleotide

<400> SEQUENCE: 16
gccgggccca ggggatccat                                                     20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:antisense
      oligonucleotide

<400> SEQUENCE: 17
cacccagatc cagcgtccca                                                     20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence:antisense
      oligonucleotide

<400> SEQUENCE: 18
atctcctgac cttgtgatcc                                                     20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence:antisense
      oligonucleotide

<400> SEQUENCE: 19
gatctcctga cctaggaaga                                                     20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence:antisense
      oligonucleotide

<400> SEQUENCE: 20
ttctcactca gttggcccat                                                     20
```

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:antisense
      oligonucleotide

<400> SEQUENCE: 21
ccaaccacca cacctgtcat                                                    20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:antisense
      oligonucleotide

<400> SEQUENCE: 22
ggacgagtaa cagctggatt                                                    20

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence:antisense
      oligonucleotide

<400> SEQUENCE: 23
gcttggctgc acccagggga tc                                                 22

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence:antisense
      oligonucleotide

<400> SEQUENCE: 24
ctctgccgct cctggacact gctgc                                              25